(12) United States Patent
Sakuma et al.

(10) Patent No.: US 9,823,563 B2
(45) Date of Patent: Nov. 21, 2017

(54) ALCOHOL COMPOUND AND METHOD FOR PRODUCING SAME, METHOD FOR PRODUCING LACTONE COMPOUND, (METH)ACRYLATE ESTER AND METHOD FOR PRODUCING SAME, POLYMER AND METHOD FOR PRODUCING SAME, AND RESIST COMPOSITION AND METHOD FOR PRODUCING SUBSTRATE USING SAME

(75) Inventors: Satoshi Sakuma, Yokohama (JP); Masashi Serizawa, Yokohama (JP); Atsushi Yasuda, Yokohama (JP); Nobuhisa Yada, Yokohama (JP); Shinichi Maeda, Yokohama (JP)

(73) Assignee: Mitsubishi Chemical Corporation, Tokyo (JP)

( * ) Notice: Subject to any disclaimer, the term of this patent is extended or adjusted under 35 U.S.C. 154(b) by 369 days.

(21) Appl. No.: 14/125,727

(22) PCT Filed: Jun. 14, 2012

(86) PCT No.: PCT/JP2012/065288
§ 371 (c)(1),
(2), (4) Date: Dec. 12, 2013

(87) PCT Pub. No.: WO2012/173209
PCT Pub. Date: Dec. 20, 2012

(65) Prior Publication Data
US 2014/0134539 A1    May 15, 2014

(30) Foreign Application Priority Data

Jun. 14, 2011    (JP) .................................. 2011-132183
Sep. 27, 2011    (JP) .................................. 2011-210667

(51) Int. Cl.
G03F 7/004        (2006.01)
G03F 7/20         (2006.01)
C07D 493/08       (2006.01)
C07D 493/18       (2006.01)
C07D 307/93       (2006.01)
(Continued)

(52) U.S. Cl.
CPC .......... *G03F 7/004* (2013.01); *C07D 307/93* (2013.01); *C07D 493/08* (2013.01); *C07D 493/18* (2013.01); *G03F 7/0041* (2013.01); *G03F 7/0392* (2013.01); *G03F 7/0397* (2013.01); *G03F 7/20* (2013.01); *G03F 7/38* (2013.01)

(58) Field of Classification Search
CPC .. C07D 307/93; C07D 493/00; C07D 493/08; C07D 493/18; G03F 7/004; G03F 7/0392; G03F 7/38
USPC ............. 549/300, 463; 430/270.1, 326, 910; 526/281, 282
See application file for complete search history.

(56) References Cited

U.S. PATENT DOCUMENTS 4,463,183 A * 7/1984 Haslanger ............... C07C 59/56
549/311
6,106,998 A    8/2000 Maeda et al.
(Continued)

FOREIGN PATENT DOCUMENTS

CN    101943861 A    1/2011
JP    11 174677       7/1999
(Continued)

OTHER PUBLICATIONS

Combined Office Action and Search Report dated Nov. 21, 2014 in Chinese Patent Application No. 201280028977.3 (with Partial English translation and English Translation of Category of Cited Documents).
(Continued)

*Primary Examiner* — John S Chu
(74) *Attorney, Agent, or Firm* — Oblon, McClelland, Maier & Neustadt, L.L.P.

(57) ABSTRACT

To provide an alcohol compound containing fewer impurities at a high yield by conducting the following steps: a hydroboration process in which a reaction mixture is obtained by reacting in a solvent a compound represented by formula (C) and a boron agent selected from a group of diborane and borane complexes; and an oxidation process in which the pH of the reaction mixture is set at 0.5 to 4, which is conducted after treating the reaction mixture with hydrogen peroxide. In the formula, $A_1$ to $A_6$ are each independently a hydrogen atom, methyl group or ethyl group, and X is an oxygen atom, sulfur atom, methylene group or ethylene group.

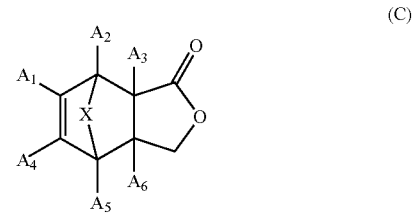

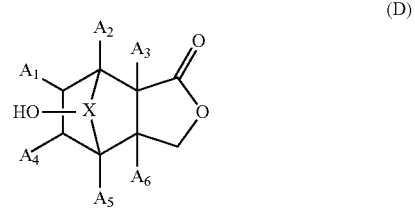

11 Claims, 2 Drawing Sheets

(51) Int. Cl.
*G03F 7/38* (2006.01)
*G03F 7/039* (2006.01)

(56) References Cited

U.S. PATENT DOCUMENTS

| | | | |
|---|---|---|---|
| 7,041,838 B2* | 5/2006 | Kamon | C07D 307/88 |
| | | | 549/295 |
| 2004/0063882 A1 | 4/2004 | Kamon et al. | |
| 2005/0032887 A1 | 2/2005 | Nakamura et al. | |
| 2005/0113538 A1* | 5/2005 | Kamon | C07D 307/88 |
| | | | 526/266 |
| 2009/0104559 A1* | 4/2009 | Houlihan | C07C 55/08 |
| | | | 430/270.1 |
| 2011/0039210 A1 | 2/2011 | Xu et al. | |

FOREIGN PATENT DOCUMENTS

| | | |
|---|---|---|
| JP | 2002 234882 | 8/2002 |
| JP | 2002 275215 | 9/2002 |
| JP | 2003 146979 | 5/2003 |
| JP | 2004 83536 | 3/2004 |
| JP | 2004 315465 | 11/2004 |
| JP | 2004 359669 | 12/2004 |
| JP | 2005 23063 | 1/2005 |
| JP | 2006 70097 | 3/2006 |
| JP | 2011 81340 | 4/2011 |
| TW | 583182 B | 4/2004 |
| TW | 200502227 A | 1/2005 |

OTHER PUBLICATIONS

Tochtermann, W. et al., "Ein Einfacher Zugang Zu 4,9-Epdxy-Octahydroazulenlactonen", Tetrahedron Letters, vol. 35, No. 8, pp. 1165-1168, (1994).
International Search Report dated Sep. 11, 2012 in PCT/JP12/065288 Filed Jun. 14, 2012.

* cited by examiner

MS SPECTRUM

ALCOHOL COMPOUND AND METHOD FOR PRODUCING SAME, METHOD FOR PRODUCING LACTONE COMPOUND, (METH)ACRYLATE ESTER AND METHOD FOR PRODUCING SAME, POLYMER AND METHOD FOR PRODUCING SAME, AND RESIST COMPOSITION AND METHOD FOR PRODUCING SUBSTRATE USING SAME

TECHNICAL FIELD

The present invention relates to the following: a (meth) acrylate ester useful as a polymerizable monomer and its production method; a lactone compound and an alcohol compound useful as an intermediate of the (meth)acrylate ester and their production methods; a polymer of the (meth) acrylate ester and its production method; a resist composition containing the polymer and a method for producing a substrate using the composition; and a novel (meth)acrylate ester and a polymer using such.

The present application is a National Stage of PCT/JP2012/065288, filed on Jun. 14, 2012. This application is based upon and claims the benefit of priority to Japanese Patent Application No. 2011-132183, filed Jun. 14, 2011, and to Japanese Application No. 2011-210667, filed Sep. 27, 2011. The entire contents of these applications are incorporated herein by reference.

DESCRIPTION OF BACKGROUND ART

In recent years, in the field of microfabrication when manufacturing semiconductor elements and liquid-crystal elements, miniaturization has advanced rapidly thanks to the development of lithographic technology. Irradiation using shorter wavelengths is usually employed for such miniaturization. In particular, conventionally used g-line (wavelength: 438 nm) or i-line (wavelength: 365 nm) ultraviolet rays are now being replaced by DUV (deep ultraviolet) light. Currently, lithographic technology using a KrF excimer laser (wavelength: 248 nm) has been introduced to the market, and lithographic technology using ArF excimer laser (wavelength: 193 nm) is being developed for applications using even shorter wavelengths. Moreover, research and development in lithographic technology has been conducted using an $F_2$ excimer laser (wavelength: 157 nm) as a next-generation technology. As for lithographic technologies slightly different from those above, technologies using electron beams or using extreme ultraviolet light (EUV light) with a wavelength around 13.5 nm have been also researched assiduously.

As for high-resolution resist for irradiation light with shorter wavelengths or for electron beams, "chemically amplified resist" containing a photoacid generator has been proposed. Improvement and development of chemically amplified resists are currently being promoted widely.

As polymers to be used for chemically amplified resists, acrylic polymers using (meth)acrylate esters as a monomer are being developed due to their highly transparent characteristics. Also, to provide various functions for resists, monomers used in such polymers have been improved vigorously on a daily basis. In recent years, as for polymerizable monomers capable of providing resists with resistance to dry etching and adhesiveness to substrates, (meth) acrylate esters with a norbornene lactone skeleton have been proposed. Various methods are being proposed for producing such lactone compounds including their intermediates (see patent publications 1 to 3, for example).

Lactone compounds are widely used as materials for functional chemicals such as pharmaceutical and agricultural products. Especially, polymerizable carboxylic acids such as (meth)acrylic acid may be added to lactone compounds with active carbon-carbon double bonds. Resist materials containing such polymer compounds formed with (meth)acrylate esters with a lactone skeleton have excellent properties such as sensitivity, resolution and etching resistance, and are useful for microfabrication by electron beams or by deep ultraviolet rays.

To obtain lactone compounds by reducing an acid anhydride having a carbon-carbon double bond in the molecule so that only the acid anhydride is selectively reduced while leaving the carbon-carbon double bond in the molecule, combinations of a reduction agent and solvent are known as follows:

(1) a combination of sodium borohydride and N,N-dimethylacetamide (patent publication 4);

(2) a combination of sodium borohydride and ethanol (non-patent publication 1); and (3) a combination of sodium borohydride and a mixed solvent of tetrahydrofuran and alcohols (patent publication 5).

In addition to being used for the above resists, (meth) acrylate esters are used as a curing component of various photocurable resin compositions such as UV-curable or electron beam-curable resins. Applications of such photocurable resin compositions are paints, ink, adhesives or the like used in plastics, paper, wood, inorganic materials and the like. Recently, applications of such photocurable resin compositions have expanded to electronics material fields such as semiconductors and liquid crystals, optoelectronics fields such as optical fibers and optical lenses, and even to medical fields.

Among such applications, polymers formed with (meth) acrylate esters with a norbornene lactone skeleton as a monomer have not been used so far.

PRIOR ART PUBLICATION

Patent Publication

[Patent Publication 1] Japanese Laid-Open Patent Publication No. 2002-234882
[Patent Publication 2] Japanese Laid-Open Patent Publication No. 2004-359669
[Patent Publication 3] Japanese Laid-Open Patent Publication No. 2011-81340
[Patent Publication 4] Japanese Laid-Open Patent Publication No. 2002-275215
[Patent Publication 5] Japanese Laid-Open Patent Publication No. 2003-146979

Non-Patent Publication

[Non-Patent Publication 1] Tetrahedron Letters, 1994, Vol. 35, No. 8, pages 1165-1168]

SUMMARY OF THE INVENTION

Problem(s) to be Solved by the Invention

Among (meth)acrylate esters with a norbornene lactone skeleton, (meth)acrylate esters, having hetero atoms such as an oxygen atom or a sulfur atom at the bridgehead of a norbornene skeleton, make it easier to control dispersion of a photoacid generator or diffusion of acid during exposure to light, and are useful as a polymerizable monomer for a polymer to be used in a chemically amplified resist. However, when such (meth)acrylate esters are produced by the production methods described in patent publications 1 and 2, desired compounds are not obtained, or problems may arise such as a low yield even if desired compounds are obtained. More specifically, in the method described in patent publication 1, a lower carboxylic acid is added to a norbornene lactone compound in the presence of an acidic catalyst to form an ester, which is then hydrolyzed to form alcohol. Then, a polymerizable monomer is obtained through reactions to form a (meth)acrylate ester. In the method described in patent publication 2, a (meth)acrylic acid is added to a norbornene lactone compound to obtain a desired polymerizable monomer. In those methods, heating at a high temperature (85 to 120° C., for example) is required in a step for adding a lower carboxylic acid or (meth)acrylic acid. Thus, the norbornene lactone compound decomposes due to reverse Diels-Alder reactions or the like, and a corresponding adduct is not obtained.

Also, in example 1 of patent publication 3, an acid anhydride with a norbornene lactone skeleton is treated by $NaBH_3$, and the obtained lactone is reacted with a $BH_3$-THF complex to form a hydroxy lactone, which is then reacted to form a (meth)acrylate ester with a norbornene lactone skeleton through esterification.

However, using the above method, the reaction yield of a hydroxy lactone as an intermediate is as low as 50%, and purification process through chromatography is conducted accordingly. Therefore, the efficiency is low and the procedure requires much labor.

Regarding production methods of lactone compounds, a combination of borohydride and a mixed solvent of tetrahydrofuran and alcohols shown in (3) leads to an excellent reaction yield when a lactone compound is produced through a reduction of acid anhydride. However, when acid anhydride is reduced using the combination shown in (3), dialcohol represented by the formula below, for example, is produced as a byproduct.

chemical formula 1

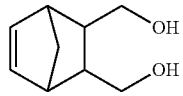

A dialcohol compound generated as a byproduct is not described in patent publication 5. When a polymerizable carboxylic acid such as (meth)acrylic acid is added to a lactone compound containing a dialcohol to synthesize a (meth)acrylate ester having a lactone skeleton, two hydroxyl groups of the dialcohol react with the carboxylic acid of (meth)acrylic acid to produce a diester. When a polymer compound is synthesized using (meth)acrylate ester having a lactone skeleton and containing a diester, the diester is copolymerized with another monomer, leading part of the polymer compound to be crosslinked. A resist material containing such a polymer compound may cause an increase in defects (failed development).

The present invention was carried out in view of the above problems. Its objective is to provide a high-yield production method to obtain alcohol compounds which are useful as an intermediate for producing (meth)acrylate esters and contain fewer impurities; and a production method using such a method, to produce (meth)acrylate esters having a norbornene lactone skeleton.

The present invention provides a high-yield production method of a lactone compound having a carbon-carbon double bond while suppressing alcohol byproducts, and a method for producing alcohol compounds using such a method.

The present invention provides alcohol compounds having a norbornene lactone skeleton and containing fewer impurities.

The present invention provides a (meth)acrylate ester having a norbornene lactone skeleton and containing fewer impurities, a polymer using the ester and a method for producing the polymer; a resist composition containing the polymer; and a method for forming a substrate with patterns formed by using the resist composition.

The present invention provides a novel compound having a norbornene lactone skeleton and a methacryloyloxy group and a novel polymer using such a novel compound.

Solutions to the Problems

The present invention relates to the following <1> through <20>.

<1> A method for producing an alcohol compound represented by formula (D) below, containing: a hydroboration process in which a reaction mixture is obtained by reacting in a solvent a compound represented by formula (C) and a boron agent selected from a group of diborane and borane complexes; and an oxidation process in which the reaction mixture is set at a pH of 0.5 to 4, which is conducted after treating the reaction mixture with hydrogen peroxide.

chemical formulas 2

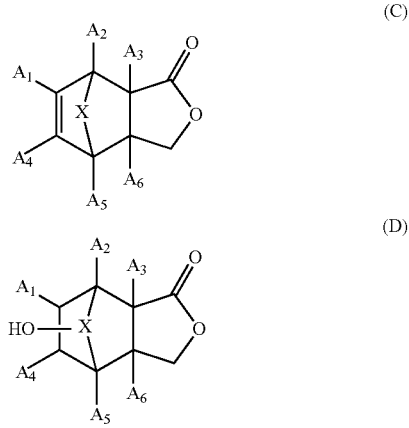

[In the above formulas, $A_1$ to $A_6$ are each independently a hydrogen atom, methyl group or ethyl group, and X is an oxygen atom, sulfur atom, methylene group or ethylene group.]

<2> A method for producing an alcohol compound described in <1>, wherein a borane dimethylsulfide complex or a borane-1,2-dimethoxyethane complex is used as the boron agent.

<3> A method for producing an alcohol compound described in <1> or <2> that includes an isolation step in which the alcohol compound represented by formula (D) above is obtained through recrystallization of the reaction mixture by adjusting the pH of the reaction mixture to be 5 to 9 after the oxidation process.

<4> A method for producing a lactone compound represented by formula (2) and/or formula (3) below by reducing the compound represented by formula (1) below with sodium borohydride, wherein the amount of sodium borohydride is set at a mole ratio of 0.7 to 0.95 relative to the compound represented by formula (1) shown below.

chemical formulas 3

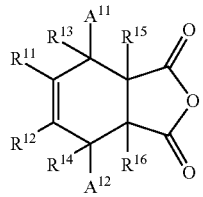
(1)

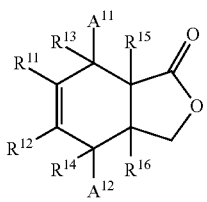
(2)

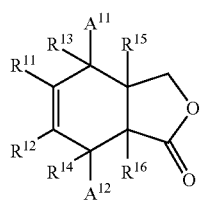
(3)

[In the formulas, $R^{11}$ to $R^{16}$ are each independently a hydrogen atom, methyl group or ethyl group; and $A^{11}$ and $A^{12}$ both are either a hydrogen atom or a bond to form —$CH_2$—, —$CH_2CH_2$—, —O—, or —S—.]

<5> A method for producing a lactone compound described in <4>, in which the compound represented by the formula (1) is a compound represented by formula (4) shown below, the lactone compound represented by the formula (2) is a lactone compound represented by formula (5) shown below, and the lactone compound represented by the formula (3) is a lactone compound represented by formula (6) shown below.

chemical formulas 4

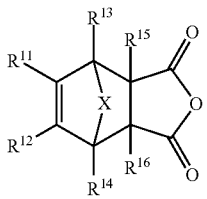
(4)

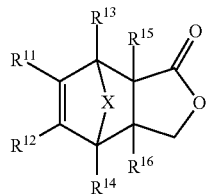
(5)

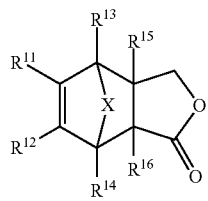
(6)

[In the above formulas, $R^{11}$ to $R^{16}$ are each independently a hydrogen atom, methyl group or ethyl group; and X is an oxygen atom, sulfur atom, methylene group or ethylene group.]

<6> A method for producing an alcohol compound described in any one of <1> through <3>, further including a step in which a compound represented by the formula (C) is produced using the method for producing a lactone compound described in <4> or <5>.

<7> A method for producing a (meth)acrylate ester, including a step in which an alcohol compound represented by formula (D) shown below is produced from the compound represented by formula (C) shown below using the method for producing an alcohol compound described in any of <1> through <3>; and a step in which a (meth)acrylate ester represented by formula (A) shown below is formed through esterification reactions of the compound represented by formula (D) shown below.

chemical formulas 5

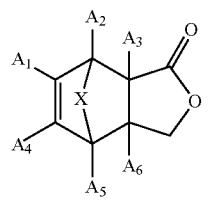
(C)

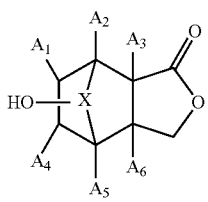
(D)

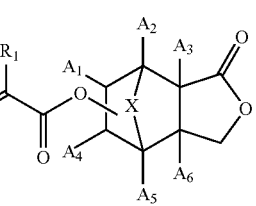
(A)

[In the above formulas, $R_1$ is a hydrogen atom or a methyl group, $A_1$ to $A_6$ are each independently a hydrogen atom, methyl group or ethyl group, and X is an oxygen atom, sulfur atom, methylene group or ethylene group.]

<8> A method for producing a (meth)acrylate ester described in <7>, further including a step in which a compound represented by the formula (C) is produced using the method for producing a lactone compound described in <4> or <5>.

<9> An alcohol compound represented by formula (D) shown below containing a compound represented by formula (ii) shown below as an impurity at a content of less than 9 mass %.

chemical formulas 6

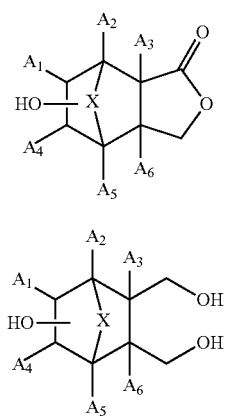

[In the above formulas, $A_1$ to $A_6$ are each independently a hydrogen atom, methyl group or ethyl group, and X is an oxygen atom, sulfur atom, methylene group or ethylene group.]

<10> A (meth)acrylate ester represented by formula (A) shown below containing a compound represented by formula (iii) shown below as an impurity at a content of less than 9 mass %.

chemical formulas 7

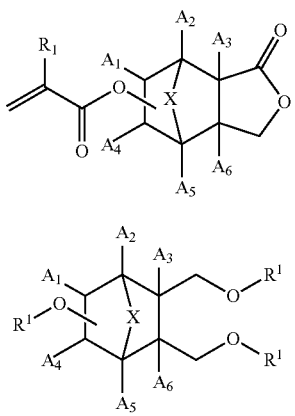

[In the above formulas, $R_1$ is a hydrogen atom or methyl group, $A_1$ to $A_6$ are each independently a hydrogen atom, methyl group or ethyl group, X is an oxygen atom, sulfur atom, methylene group or ethylene group, and $R^1$ is an acryloyl group or methacryloyl group.]

<11> A (meth)acrylate ester, represented by formula (A') shown below, in which the peak area of an impurity (X), having a molecular weight of 308 and producing methacrylic acid when decomposed during storage, is set at no more than 0.3% of the peak area of the (meth)acrylate ester (A') in a chromatogram measured by high performance liquid chromatography.

<12> A (meth)acrylate ester, represented by formula (A') shown below, in which the amount of methacrylic acid is set at no more than 0.04 mole ratio to the (meth)acrylate ester (A'), and the peak area of an impurity (X), having a molecular weight of 308 and producing methacrylic acid when decomposed during storage, is set at no more than 0.3% of the peak area of the (meth)acrylate ester (A') in a chromatogram measured by high performance liquid chromatography.

chemical formula 8

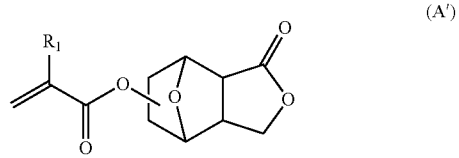

[In the formula, $R_1$ is a hydrogen atom or a methyl group.]

<13> A (meth)acrylate ester represented by formula (A) shown below containing a compound represented by formula (v) shown below as impurities at a content of less than 9 mass %.

chemical formulas 9

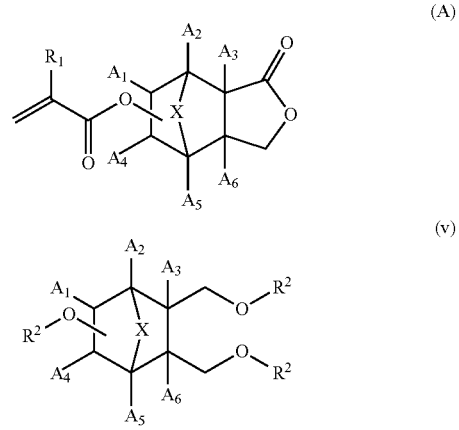

[In the formulas, $R_1$ is a hydrogen atom or a methyl group, $A_1$ to $A_6$ are each independently a hydrogen atom, methyl group or ethyl group, X is an oxygen atom, sulfur atom, methylene group or ethylene group, and $R^2$ is a hydrogen atom, acryloyl group or methacryloyl group.]

<14> A polymer obtained by polymerizing at least one type of monomer, and the monomer contains the (meth)acrylate ester described in any one of <10> through <13>.

<15> A polymer obtained by polymerizing at least two types of monomers, and the monomers contain the (meth)acrylate ester described in any one of <10> through <13> and another (meth)acrylate ester excluding those in any one of <10> through <13>.

<16> A method for producing a polymer including a step in which a monomer that contains the (meth)acrylate ester described in any one of <10> through <13> is polymerized.

<17> A resist composition containing the polymer described in <14> or <15> and a compound that generates acid when irradiated by active light or radial rays.

<18> A method for producing a substrate with patterns formed thereon including a step in which a resist film is formed by applying the resist composition described in <17> on the surface of a substrate to be fabricated, a step in which the resist film is exposed to light, and a step in which the exposed resist film is developed using a developing solution.

<19> A compound represented by formula (iii) shown below.

chemical formula 10

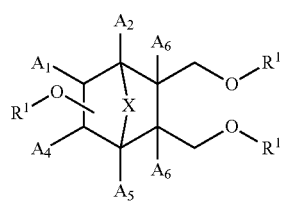

(iii)

[In the formula, $A_1$ to $A_6$ are each independently a hydrogen atom, methyl group or ethyl group, X is an oxygen atom, sulfur atom, methylene group or ethylene group, and $R^1$ is an acryloyl group or methacryloyl group.]

<20> A polymer obtained by using the compound described in <19> as a monomer.

Effects of the Invention

According to the embodiments of the present invention, an alcohol compound useful as an intermediate of a (meth) acrylate ester is produced at a high yield, and a (meth) acrylate ester having a norbornene lactone skeleton is efficiently produced using such an alcohol compound.

The embodiments of the present invention provide a lactone compound having a carbon-carbon double bond while suppressing production of dialcohol byproducts.

The embodiments of the present invention provide an alcohol compound having a norbornene lactone skeleton and containing fewer impurities.

The embodiments of the present invention provide a (meth)acrylate ester having a norbornene lactone skeleton and containing fewer impurities, which subsequently produces a polymer and a resist composition with excellent properties. Also obtained is a substrate with excellent patterns formed using such a resist composition.

The embodiments of the present invention provide a novel compound having a norbornene lactone skeleton and a methacryloyloxy group as well as a novel polymer formed using such a novel compound.

MODE TO CARRY OUT THE INVENTION

Figure 1:
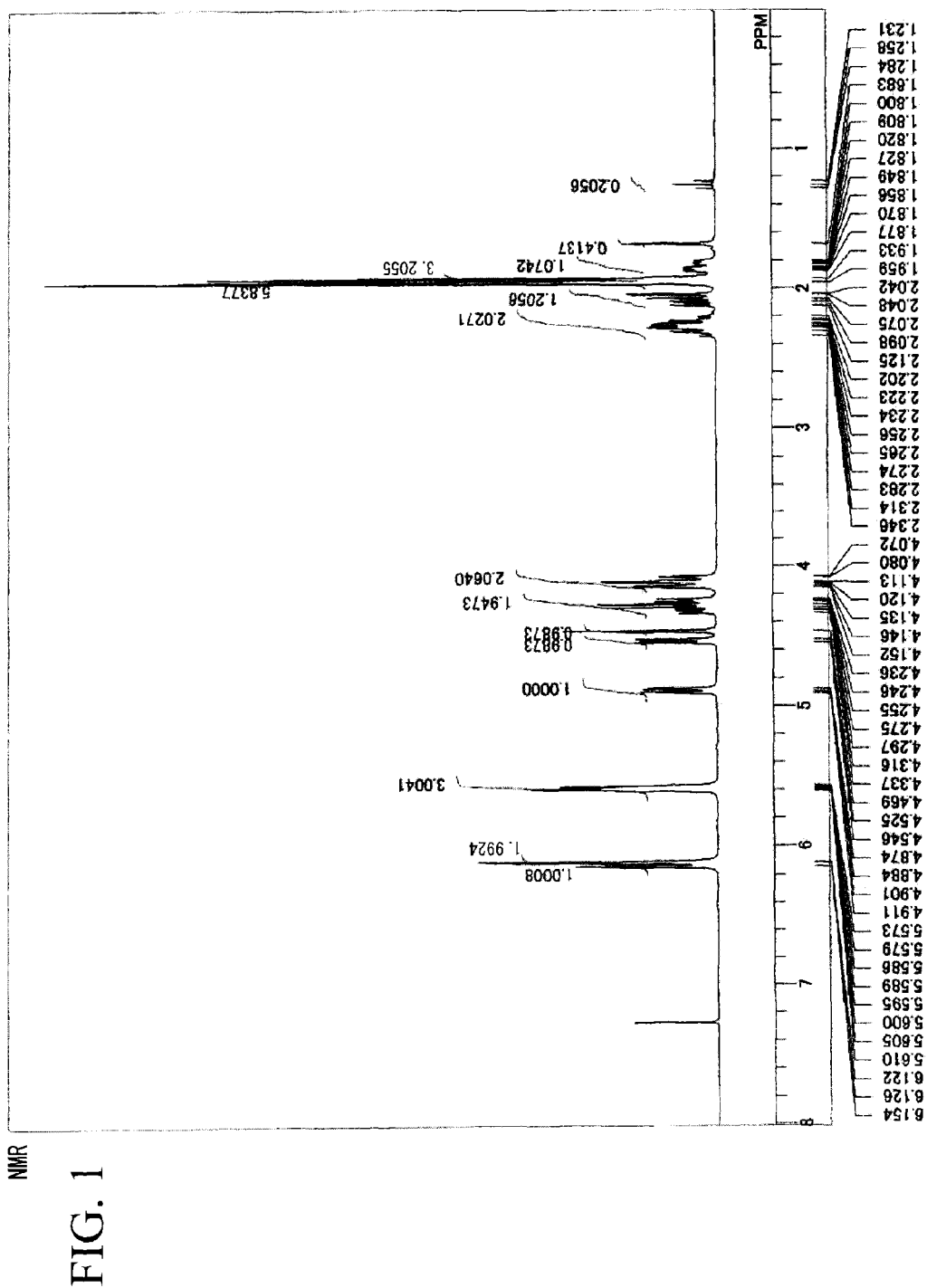
FIG. 1 is $^1$H-NMR spectrum of a compound (iii-1) obtained in an example.

In the following, the present invention is described in detail.

In the present application, "(meth)acrylic acid" means acrylic acid or methacrylic acid.

In the following, general formula (A) may be referred to simply as formula (A) (the same applies to other formulas.)

A compound represented by formula (A) may be referred to as compound (A) (the same applies to other compounds represented by other formulas.)

<Method (I) for Producing Alcohol Compound>

In the following, an embodiment is described regarding a method for producing an alcohol compound (D) represented by formula (D).

The method for producing alcohol compound (D) according to the present embodiment includes a hydroboration process for obtaining a reaction mixture through chemical reactions of a lactone compound (C) represented by formula (C) and a boron agent in a solvent, a hydrogen-peroxide treatment process, and an oxidation process.

chemical formulas 11

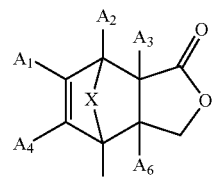

(C)

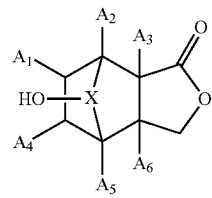

(D)

[In the formulas, $A_1$ to $A_6$ are each independently a hydrogen atom, methyl group or ethyl group, and X is an oxygen atom, sulfur atom, methylene group or ethylene group.]

In formulas (C) and (D), $A_1$ to $A_6$ are preferred to be each independently a hydrogen atom or a methyl group. The total number of methyl and ethyl groups in the molecule may be any number from 0 to 6, but 0 to 2 is preferred, and 0 to 1 is especially preferred, when a polymer having a structural unit derived from compound (D) is used as a resist resin. "X" is preferred to be an oxygen atom or a methylene group.

Lactone compound (C) is produced using a well-known method. However, it is preferred to produce lactone compound (C) by later-described method (II) for producing a lactone compound and to conduct a hydroboration process of the present embodiment using such a lactone compound.

(Hydroboration Process)

A hydroboration process is carried out using a boron agent selected from a group of diborane and borane complexes. Preferred boron agents are diborane, borane-dimethylsulfide complex, borane-1,2-dimethoxyethane complex (hereinafter referred to as borane-DME complex), borane-THF complex, borane-tetrahydropyran complex and the like. Among them, borane-dimethylsulfide complex and borane-DME complex are preferred considering reaction speed or reduction of byproducts.

The amount of a boron agent in terms of a boron atom is preferred to be at least 0.5 molar equivalent to lactone compound (C) to complete the hydroboration process, and no more than 2.0 molar equivalent to lactone compound (C) to suppress byproducts.

A boron agent may be such that is synthesized and isolated in advance, or may be such that is generated in the system. To produce a boron agent in the system is well known. For example, to produce a borane complex, sodium borohydride is reacted with concentrated sulfuric acid or dimethylsulfate at a mole ratio of 0.5 in the presence of a solvent to form a complex.

Examples of a hydroboration process of the present embodiment are as follows: an isolated boron agent or a boron agent generated in the system is dropped into a solution prepared by dissolving lactone compound (C) in advance; a solution prepared in advance by dissolving lactone compound (C) is dropped into a boron agent isolated or generated in the system; sulfuric acid or dimethyl sulfate is dropped into a solvent (such as DME) to form a borane complex prepared by adding lactone compound (C) and sodium borohydride; or the like.

A solvent to dissolve lactone compound (C) in advance is not limited specifically as long as it does not react with a boron agent, and DME and tetrahydrofuran (hereinafter referred to as THF) are preferred because of the solubility of lactone compound (C) and the ease of handling.

In either method above, heat is generated during the dropping process. To control reactions, it is preferred to perform dropping at a certain flow rate so that the temperature of the reaction mixture during the dropping process is kept at 40° C. or lower, preferably at −10 to 30° C.

[Hydrogen Peroxide Treatment]

A borohydride of lactone compound (C) is contained in the reaction mixture after the completion of the hydroboration process. When the borohydride is treated by hydrogen peroxide, alcohol compound (D) is obtained.

To perform hydrogen peroxide treatment, a well-known method of forming alcohol from a borohydride is used. More specifically, after the hydroboration process is finished, water is added to the reaction mixture, which is then treated by hydrogen peroxide in the presence of a base.

[Oxidation Process]

During the hydroboration process, a compound represented by formula (i) is generated as a byproduct, a portion of which is a compound represented by formula (ii).

In the present process, alcohol compound (D) is obtained from a compound represented by formula (i) by performing an oxidation process after the completion of the hydroboration process. More specifically, the reaction mixture after the completion of the hydroboration process is treated by hydrogen peroxide, and acid is added to set the pH at 0.5 to 4. Considering the processing speed, the pH is preferred to be adjusted to be 3 or lower, more preferably 2 or lower. Considering the amount of a base for neutralization after the oxidation process, the pH is preferred to be adjusted to be 0.8 or higher, more preferably 1 or higher.

Examples of an acid to be added to the reaction mixture in the present process are mineral acids (hydrochloric acid, sulfuric acid, nitric acid, phosphoric acid and the like), acidic ion-exchange resins and the like. They may be used alone, or two or more may be combined. Sulfuric acid is preferred due to the ease of handling.

chemical formulas 12

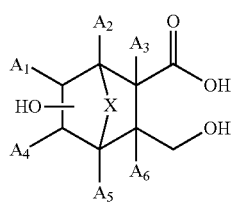

(i)

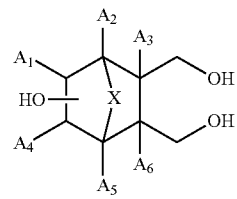

(ii)

$A_1$ to $A_6$ and X in formulas (i) and (ii) are each the same as $A_1$ to $A_6$ and X in formula (D) including preferred examples.

[Isolation Process]

Isolation of alcohol compound (D) from the reaction mixture after the oxidation process is not limited to any specific method. However, considering the high solubility of alcohol compound (D) in water, it is preferred to evaporate the solvent used for the reaction, to add an organic solvent so that sodium sulfate generated as a byproduct is deposited and filtered, and then to evaporate the organic solvent again.

Examples of an organic solvent above are acetone, methanol, ethanol, acetonitrile and the like. Since moisture may affect the esterification process in later-described step (3), ethanol is preferred because its azeotropic ability with water is high and it is easier to be removed from alcohol compound (D).

The water content of alcohol compound (D) in step (3) is preferred to be set at 5000 ppm or less, more preferably at 2000 ppm or less. The water content is adjusted by the amount of an organic solvent in the azeotropic process or the number of times to conduct azeotropic procedures. The amount of an organic solvent in the azeotropic process or the number of times for the procedure is not limited specifically, and may be selected properly. Also, the water content is measured using a Karl Fischer moisture meter.

In a preferred embodiment of the isolation process, the pH of the reaction mixture after the oxidation process is adjusted to be 5 to 9 for recrystallization so that alcohol compound (D) is isolated. The pH is more preferred to be 6 to 8. To adjust the pH in the above range, for example, it is an option to neutralize the reaction mixture using ammonia, aqueous ammonia, oxides of alkali metals and alkaline earth metals, hydroxides, carbonates, hydrogen carbonates and the like. Considering the yield of purification, neutralization by ammonia or aqueous ammonia is more preferred.

<Alcohol Compound>

According to an embodiment of the present invention, alcohol compound (D) with a low content of impurities is obtained by performing an oxidation process after the hydroboration process.

In the present application, the content of impurities in alcohol compound (D) is measured in the dry powder of alcohol compound (D) with a purity rate of at least 90 mass %.

More specifically, alcohol compound (D) is obtained to have a content of compound (ii) of less than 9 mass %, preferably 6 mass % or less. Such alcohol compound (D) is preferred to contain substantially no compound (i).

The content of impurities in the alcohol compound is measured by high performance liquid chromatography (HPLC) using a UV detector. In the present application, "substantially no content" means the content is lower than the detection limit. Usually, the detection limit is no higher than 0.01 mass % in liquid chromatography using a UV detector.

Such an alcohol compound with significantly low impurity content is especially suitable as a raw material for synthesizing resist polymers.

Here, compound (D) and compounds (i) and (ii) may have isomers, and the amounts of those compounds in the present application mean the total amounts including isomers.

<Method (II) for Producing Lactone Compound>

In this embodiment, a method is described for producing a lactone compound represented by formula (2) or (3) below.

In the method for producing a lactone compound of the present embodiment, a compound represented by formula (1) is reduced by sodium borohydride to produce either a lactone compound represented by formula (2) or a lactone compound represented by formula (3), or both of such compounds.

chemical formulas 13

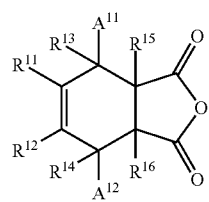
(1)

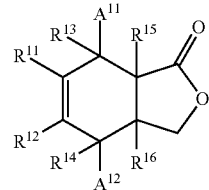
(2)

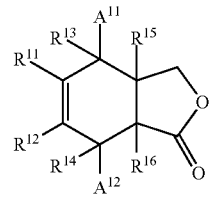
(3)

[In the formulas, $R^{11}$ to $R^{16}$ are each independently a hydrogen atom, methyl group or ethyl group; and $A^{11}$ and $A^{12}$ are both a hydrogen atom, or a bond to form —$CH_2$—, —$CH_2CH_2$—, —O— or —S—.]

Specifically, the present method includes following steps (a) to (c).

(a) A compound represented by formula (1) shown below is reduced by sodium borohydride to obtain a compound represented by formula (7) shown below or a compound represented by formula (8) shown below (reduction process).

(b) By adding a pH adjustment agent to a reaction mixture obtained in step (a), unreacted sodium borohydride decomposes so that the reaction is terminated, while a lactone compound represented by formula (2) shown below and/or a lactone compound represented by formula (3) shown below is obtained (pH adjustment process). Namely, a ring-closure reaction of a compound represented by formula (7) or (8) is performed in the pH adjustment process.

(c) The lactone compound obtained in step (b) is extracted and washed with water or the like if necessary (purification process).

chemical formulas 14

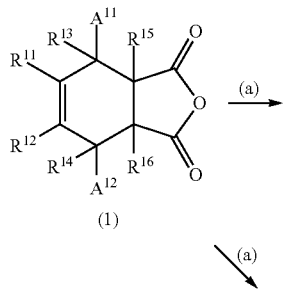 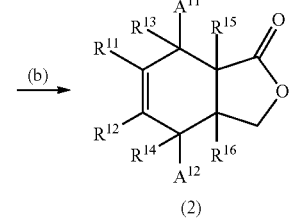
(1) (7) (2)

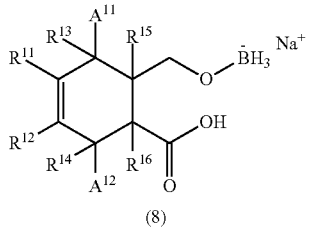 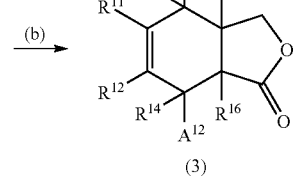
(8) (3)

[Step (a)]

(Compound Represented by Formula (1))

Examples of a compound represented by formula (1) are compounds shown below.

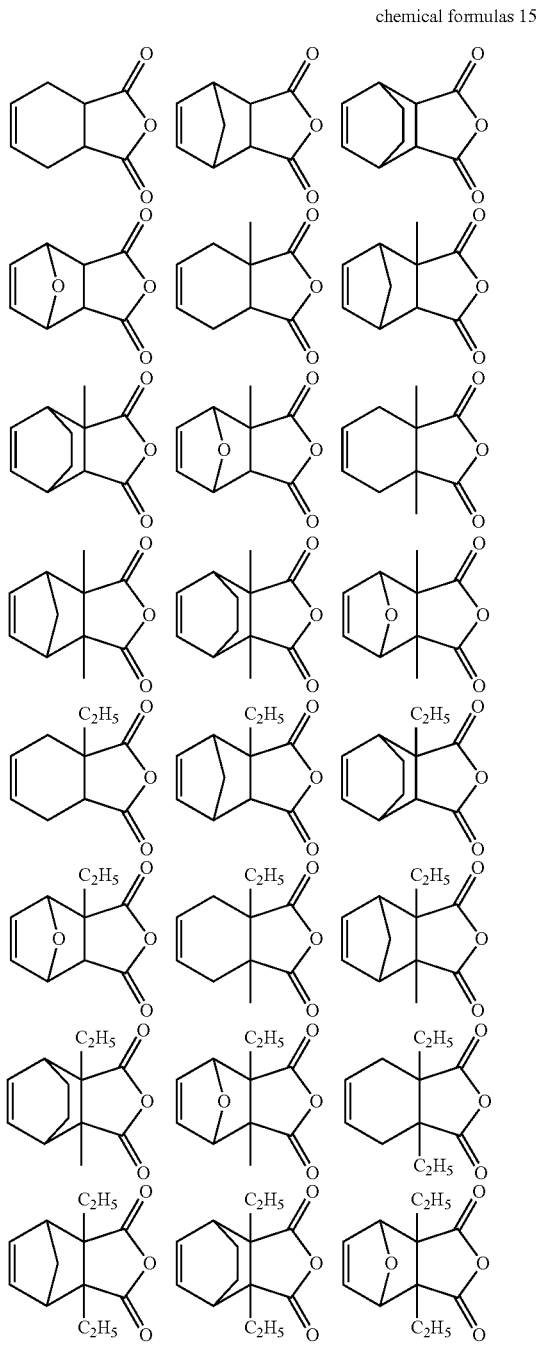

As an example of a compound represented by formula (1), a compound represented by formula (4) is preferred since the reaction progresses with an excellent reaction yield.

In formula (4), $R^{11}$ to $R^{16}$ are each independently a hydrogen atom, methyl group or ethyl group, and X is an oxygen atom, sulfur atom, methylene group or ethylene group. X is preferred to be an oxygen atom or a methylene group.

Examples of a compound represented by formula (4) are 5-norbornene-2,3-dicarboxylic anhydride, 2-methyl-5-norbornene-2,3-dicarboxylic anhydride, 4,10-dioxatricyclo[5.2.1.0$^{2,6}$]deca-8-en-3,5-dione, or the like.

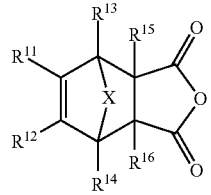

(4)

Examples of a compound represented by formula (1) are synthesized by Diels-Alder addition reactions with 1,3-diene and maleic anhydride.

Examples of 1,3-diene are 1,3-butadiene, cyclopentadiene, 1-methylcyclopentadiene, 1,3-dimethylcyclopentadiene, 1-ethylcyclopentadiene, 1-ethyl-3-methylcyclopentadiene, 1,3-diethylcyclopentadiene, 1,3-cyclohexadiene, 1-methyl-1,3-cyclohexadiene, 1,3-dimethyl-1,3-cyclohexadiene, 1-ethyl-1,3-cyclohexadiene, 1-ethyl-3-methyl-1,3-cyclohexadiene, 1,3-diethyl-1,3-cyclohexadiene, furan, 1-methylfuran, 1,3-dimethylfuran, 1-ethylfuran, 1-ethyl-3-methylfuran and 1,3-diethylfuran. Among those, 1,3-diene may be appropriately selected depending on the desired product. Further, commercially available compounds may be used for those represented by formula (1).

(Sodium Borohydride)

Commercially available agents are used for sodium borohydride. The amount of sodium borohydride is preferred to be at least 0.7 mol, preferably at least 0.8 mol, per 1 mol of a compound represented by formula (1) to enhance the conversion rate (improving reaction yield). The amount of sodium borohydride is preferred to be 0.95 mol or less, preferably 0.9 mol or less, per 1 mol of a compound represented by formula (1) to suppress dialcohol byproducts.

(Solvent)

Reduction of a compound represented by formula (1) using sodium borohydride is usually conducted in a solvent.

In the present embodiment, examples of such a solvent are alcohols (methanol, ethanol, propanol, isopropanol, 1-butanol, 2-butanol, isobutanol, t-butanol and the like), ethers (diethyl ether, methyl-t-butyl ether, diisopropyl ether, tetrahydrofuran, dimethoxyethane and the like), esters (ethyl acetate, γ-butyrolactone and the like), nitriles (acetonitrile and the like), amides (N,N-dimethylformamide, N,N-dimethylacetamide and the like), and hydrocarbons (toluene, xylene, hexane and the like). Solvents may be used alone, or two or more may be combined.

As for a solvent, the following examples are preferred because of high reaction rates, excellent solubility of sodium borohydride and a compound represented by formula (1) in such solvents, and a small amount of dialcohol byproducts: tetrahydrofuran, methanol, N,N-dimethylformamide, N,N-dimethylacetamide, a mixed solvent of tetrahydrofuran and alcohols and a mixed solvent of dimethoxyethane and alcohols. Among those, a mixed solvent of tetrahydrofuran and methanol as well as a mixed solvent of dimethoxyethane and alcohol are especially preferred, since a desired lactone compound is obtained at a high reaction yield while dialcohol byproducts are well suppressed when such solvents are used.

The amount of a mixed solvent to be used may be determined properly depending upon the type of alcohol. Usually, the amount is preferred to be at least 0.1 mol, preferably at least 0.5 mol, per 1 mol of sodium borohydride from the viewpoint of reaction speed. Usually, the amount of a mixed solvent is preferred to be 20 mol or less, preferably 10 mol or less, per 1 mol of sodium borohydride considering the stability of sodium borohydride.

The amount of a solvent is preferred to be 100 parts by mass or less, preferably 33 parts by mass or less, even more preferably 20 parts by mass or less, per 1 part by mass of a compound represented by formula (1) from a viewpoint of reaction speed. The amount of a solvent is preferred to be at least 0.5 parts by mass, preferably at least 1 part by mass, even more preferably 1.5 parts by mass, per 1 part by mass of a compound represented by formula (1) to keep the viscosity of the reaction mixture from deteriorating.

(Reduction Process)

The reduction process in step (a) progresses, for example, by putting sodium borohydride and a solvent in a reactor, and by continuously or intermittently dropping a compound represented by formula (1) dissolved in a solvent. Also, the reduction process progresses by putting a solvent and a compound represented by formula (1) in a reactor and by continuously or intermittently dropping sodium borohydride or its suspension.

When a mixed solvent of two or more types is used, such solvents may be dropped separately, or they may be combined and dropped.

(Reaction Conditions)

The optimal reaction temperature varies depending on the dropping rate of the material solution or its concentration. Usually, the reaction temperature is preferred to be at least −50° C., more preferably at least −40° C., even more preferably at least −30° C., from a viewpoint of reaction speed. The reaction temperature is preferred to be 100° C. or lower, more preferably 70° C. or lower, even more preferably 40° C. or lower, from the viewpoint of preventing side reactions.

The duration for dropping is preferred to be at least 0.1 hour, more preferably at least 0.2 hour, even more preferably at least 0.5 hour, considering the ease of controlling temperature. The duration for dropping is preferred to be 30 hours or shorter, more preferably 20 hours or shorter, even more preferably 10 hours or shorter, to keep the viscosity of the reaction mixture from deteriorating. Such dropping duration is preferred to be 0.1 to 30 hours, more preferably 0.2 to 20 hours, even more preferably 0.5 to 10 hours. If necessary, ripening time of 20 hours or shorter may be provided after the dropping is finished.

The reaction is conducted while avoiding moisture as much as possible. For that matter, the reactor and the reservoir of material solutions are preferred to be kept under an inert gas atmosphere. Examples of inert gas are not limited specifically as long as the gas does not hamper the smooth progress of the reaction; for example, helium gas, nitrogen gas, argon gas or the like may be used.

(Step (b))
(pH Adjustment Agent)

At least acid is used for a pH adjustment agent. Examples of acid are mineral acids (hydrochloric acid, sulfuric acid, nitric acid, phosphoric acid and the like), acidic ion-exchange resins and the like. A single pH adjustment agent may be used, or two or more agents may be combined. For mass syntheses, sulfuric acid is preferred as a pH adjustment agent due to the ease of handling.

When a pH adjustment agent is mixed with water for dropping, the concentration of the pH adjustment agent in the mixture (percentage by mass) is preferred to be at least 0.1 mass %, more preferably at least 5 mass %, because intramolecular cyclization reactions progress efficiently at such percentages. The concentration of the pH adjustment agent (percentage by mass) is preferred to be 70 mass % or lower, more preferably 50 mass % or lower, from a viewpoint of preventing foaming.

The concentration of the pH adjustment agent is preferred to be 0.1 to 70 mass %, more preferably 5 to 50 mass %.

(Adding pH Adjustment Agent)

In step (b), a pH adjustment agent and water are added to the reaction mixture obtained in step (a) to acidify the aqueous phase of the reaction mixture so that the reduction process is terminated. The amount of the pH adjustment agent is properly adjusted according to the pH of the aqueous phase after the pH adjustment agent has been added (a pH at 20° C.). The pH is preferred to be set at 4.0 or lower, more preferably at 3.0 or lower, even more preferably at 2.0 or lower, to suppress the hydrolysis of the lactone compound. Also, the pH is set at no less than 0.1. Accordingly, a lactone compound represented by formula (2) and/or (3) is obtained. The pH is preferred to be at least 1.0 to remove acid efficiently.

The pH of the aqueous phase after adding the pH adjustment agent is preferred to be 0.1 to 4.0, more preferably 1.0 to 3.0, even more preferably 1.0 to 2.0.

After adding the pH adjustment agent, it is preferred to set retention time of at least 0.01 hour but no longer than 50 hours if necessary. In so setting, intramolecular cyclization reactions progress efficiently. Such retention time is more preferred to be set for 0.1 to 40 hours.

(Lactone Compound)

Examples of a lactone compound represented by formula (2) or (3) are as follows.

chemical formulas 17

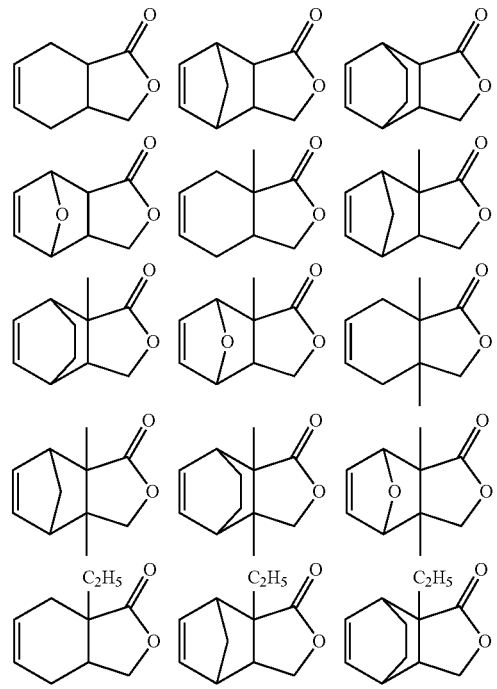

-continued

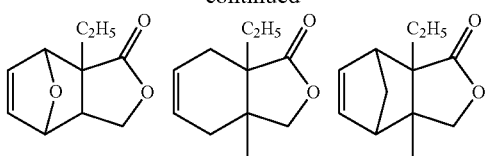
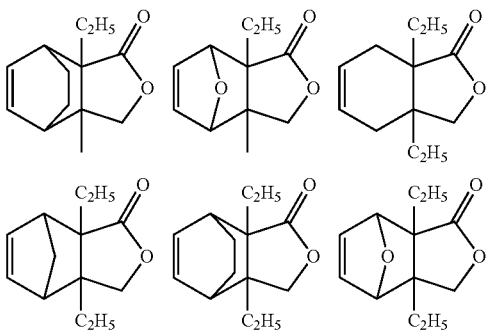

chemical formulas 18

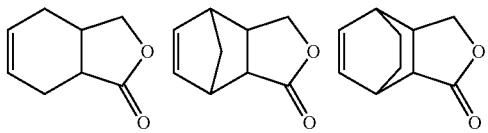
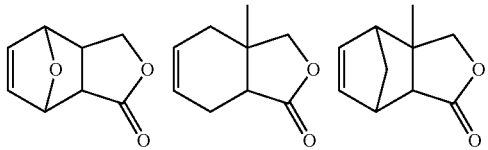
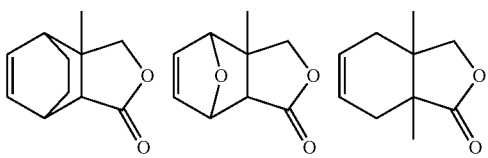
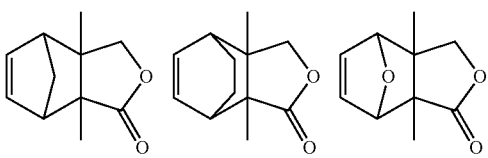
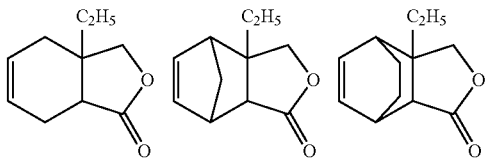
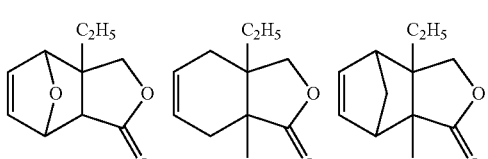
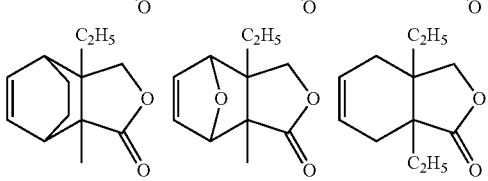

-continued

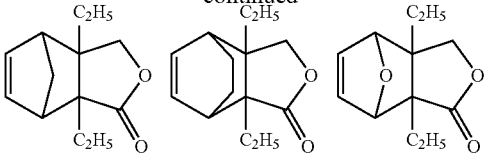

As for a lactone compound represented by formula (2), it is preferred to be one represented by formula (5) from the viewpoint of an excellent yield. As for a lactone compound represented by formula (3), it is preferred to be one represented by formula (6) from the viewpoint of an excellent yield. In formula (5), $R^{11}$ to $R^{16}$ are each independently a hydrogen atom, methyl group or ethyl group, and X is an oxygen atom, sulfur atom, methylene group or ethylene group.

chemical formulas 19

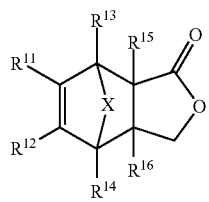 (5)

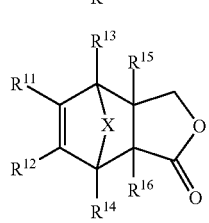 (6)

(Step (c))

Extraction of a lactone compound is carried out by using an organic solvent capable of dissolving the lactone compound. Examples of an organic solvent to be used for extraction are ethers (dimethyl ether, methyl-t-butyl ether, diisopropyl ether and the like), ketones (methyl-n-propyl ketone, methyl-n-butyl ketone, methyl isobutyl ketone and the like), aromatic hydrocarbons (toluene, xylene and the like), and esters (ethyl acetate and the like). The organic solvent may be used alone, or two or more solvents may be combined.

The amount of an organic solvent is not limited specifically. However, considering efficient extraction, the amount is preferred to be at least 0.05 times but no more than 20 times the amount of the lactone compound. Extraction may be divided into multiple procedures.

The amount of acid or the like used as a pH adjustment agent is reduced by washing a reaction mixture or extraction mixture with water.

After the reaction mixture or extraction mixture is obtained, the desired lactone compound may be purified through distillation, recrystallization, chromatography or the like. If the purity is high, a purification procedure is not necessary. For example, the extraction mixture is concentrated to obtain the desired lactone compound.

[Effects]

In the method for producing a lactone compound of the present embodiment, the amount of sodium borohydride is set at 0.7 to 0.95 mole ratio to a compound represented by formula (1). Accordingly, a lactone compound with a carbon-carbon double bond is produced at a high yield while production of dialcohol byproducts is suppressed. In particular, dialcohol byproducts are suppressed to be less than 1 mass % using the method for producing a lactone compound according to the present embodiment.

When a polymerizable carboxylic acid such as (meth)acrylic acid is added to a lactone compound having a carbon-carbon double bond in which dialcohol byproducts are suppressed, and a (meth)acrylate ester having a lactone skeleton is synthesized, production of diester byproducts is suppressed and a (meth)acrylate ester with a lactone skeleton is produced at a high yield. Thus, resist material is obtained with a significantly low rate of defects (such as developing failure), which are caused when such a diester compound is copolymerized with other monomers and part of the polymer compound is cross-linked.

The lactone compound with a carbon-carbon double bond according to the manufacturing method of the present embodiment is useful as a material for a (meth)acrylate ester with a lactone skeleton, which is the material for a polymer compound to be used as a resist material.

(Dialcohol)

In the method for producing a lactone compound of the present embodiment, dialcohol byproducts are suppressed. Such a dialcohol is a compound represented by formula (9).

chemical formula 20

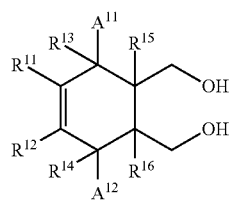

(9)

In the formula, $R^{11}$ to $R^{16}$, $A^{11}$ and $A^{12}$ are the same as in formula (1). Examples of such a compound represented by formula (9) are as follows.

chemical formulas 21

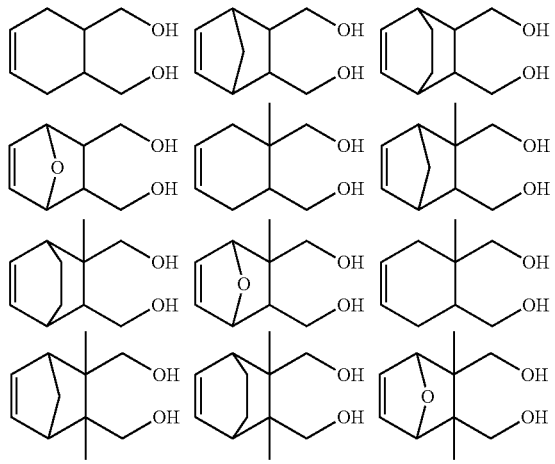

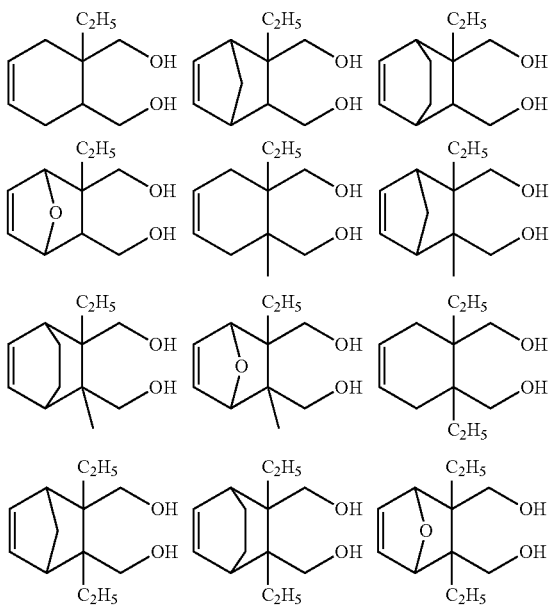

<Method for Producing (Meth)Acrylate Ester>

A method for producing (meth)acrylate ester (A) is described according to an embodiment of the present invention.

A (meth)acrylate ester represented by formula (A) is produced according to the production method of the present invention. The method includes steps (1) to (3) below.

Step (1): to produce a compound represented by formula (C) (may also be referred to as lactone compound (C)) from a compound represented by formula (B) (may also be referred to as acid anhydride (B)) through a reduction reaction.

Step (2): to obtain a compound represented by formula (D) (may also be referred to as alcohol compound (D)) from lactone compound (C) through a hydroboration process.

Step (3): to obtain compound (A) represented by formula (A) from alcohol compound (D) through esterification reaction.

chemical formulas 22

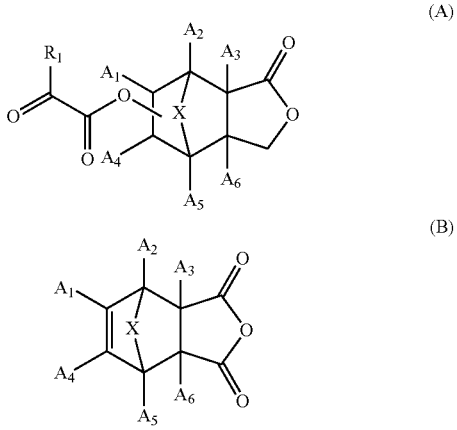

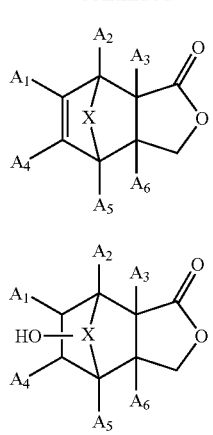

[In the formula, $R_1$ is a hydrogen atom or a methyl group, $A_1$ to $A_6$ are each independently a hydrogen atom, methyl group or ethyl group, and X is an oxygen atom, sulfur atom, methylene group or ethylene group.]

In formulas (A) to (D), $A_1$ to $A_6$ are each preferred to be independently a hydrogen atom or a methyl group. The total number of methyl and ethyl groups in the molecule may be any number from zero to six, but 0 to 2 is preferred, and 0 to 1 is especially preferred, when a polymer having a structural unit derived from compound (D) is used as a resist resin. X is preferred to be an oxygen atom or a methylene group.

[Step (1) (Reduction Process)]

In step (1), lactone compound (C) is obtained from acid anhydride (B) through a reduction reaction.

The present step is preferred to be conducted by method (II) for producing a lactone compound described above. Formula (B) corresponds to an example in which $A^{11}$ and $A^{12}$ are connected in formula (I).

The present step may also be conducted in method (III) for producing a lactone compound described below.

<Method (III) for Producing Lactone Compound>

Acid anhydride (B) is easily synthesized using a well-known method such as Diels-Alder reaction of maleic anhydride and 1,3-diene such as furan. Alternatively, a commercially available compound may also be used. Examples of 1,3-diene are the same as in method (II) for producing a lactone compound described above.

A reduction reaction is carried out by using a reduction agent. Examples of a reduction agent to be used in the present step are metal hydrides and metal hydride complexes. Such compounds are not limited to a specific type, and include the following: borane.dimethyl sulfide, diisobutylaluminum hydride, sodium borohydride, lithium borohydride, potassium borohydride, zinc borohydride, lithium tri-s-butylborohydride, potassium tri-s-butylborohydride, lithium triethylborohydride, lithium aluminum hydride, lithium tri-t-butoxyaluminumhydride, sodium bis(methoxyethoxy)aluminum hydride, and the like. Among those, sodium borohydride is preferred because handling is easier and side reactions are suppressed.

The amount of a reduction agent to acid anhydride (B) is preferred to be set at 0.5 mol equivalent or more to complete the reaction, and 1.5 mol equivalent or less to suppress side reactions. It is especially preferred that the amount of a reduction agent be set at 0.7 to 0.95 mol equivalents to acid anhydride (B).

A reduction reaction is usually carried out in the presence of a solvent. Aprotic polar solvents are preferred to be used as solvents for reduction reactions. Examples of aprotic polar solvents are alcohol-based solvents such as methanol and ethanol; ether-based solvents such as diethyl ether, tetrahydrofuran, dimethoxyethane and diglyme and triglyme; ester-based solvents such as ethyl acetate and γ-butyrolactone; nitrile-based solvents such as acetonitrile; amide-based solvents such as N,N-dimethylformamide (DMF), N,N-dimethylacetamide (DMAc) and N-methylpyrrolidone; hydrocarbon-based solvents such as toluene and hexane; and dimethyl sulfoxide. Those solvents may be used alone, or two or more solvents may be combined.

Because reduction reactions of acid anhydride (B) progress promptly, at least one of DMF or DMAc, especially DMAc, is preferred to be contained as an aprotic polar solvent.

Through a reduction reaction of acid anhydride (B), a compound represented by formula (E) shown below (a compound produced when the lactone ring of lactone compound (C) is opened, hereinafter referred to as compound (E)) is obtained. Therefore, to obtain lactone compound (C), ring-closure reactions by acid are necessary.

Namely, lactone compound (C) is obtained in step (1) by conducting a reduction process of acid anhydride (B) and through a ring-closure reaction by acid onto the resulting product (compound (E)).

Acids used for ring-closure reactions are sulfuric acid, hydrochloric acid, nitric acid, phosphoric acid and the like. Acidic ion-exchange resin may also be used. At this time, to conduct ring-closure reactions efficiently, the pH at 20° C. of the reaction mixture after acid is added is preferred to be 2.0 or lower.

chemical formula 23

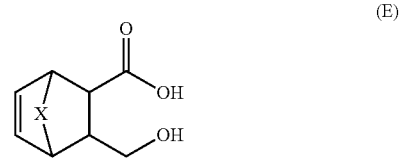

[In the formula, X is an oxygen atom, sulfur atom, methylene group or ethylene group.]

To extract lactone compound (C) from the reaction mixture obtained above, extraction using an organic solvent is usually carried out. An organic solvent used for that purpose is not limited specifically as long as it is separable from water and dissolves lactone compound (C). For example, methyl isobutyl ketone (MIBK), cyclohexanone, t-butyl methyl ether (MTBE) or the like is used.

After the solvent used for the extraction is distilled, it is an option for lactone compound (C) to be used as extracted or to be purified for the next step. The purification method is not limited specifically but is properly selected from standard methods such as column chromatography, crystallization, distillation and the like.

(Step (2) (Hydroboration Process))

From lactone compound (C), alcohol compound (D) is obtained through a hydroboration process in step (2).

Method (I) for producing alcohol compounds described above is employed for this step.

(Step (3) (Esterification Process))

From alcohol compound (D) produced in step (2), compound (A) is obtained through an esterification reaction in the present step.

Methods for esterification reactions are not limited specifically, and esterification will progress by any well-known esterification method without problems. Methods such as follows may be employed: a method for reacting (meth)acrylic acid with alcohol compound (D) in the presence of an acidic catalyst or condensing agent; a method for reacting a (meth)acrylic acid halide or (meth)acrylic anhydride with compound (D) in the presence of a base; and a method for reacting lower alkyl esters of (meth)acrylic acid with alcohol compound (D) in the presence of a metal catalyst through transesterification reactions.

Considering production yields, it is preferred to employ a method for reacting a (meth)acrylate halide or (meth)acrylic anhydride with compound (D) in the presence of a base or a method for reacting lower alkyl esters of (meth)acrylic acid with alcohol compound (D) in the presence of a metal catalyst through transesterification reactions. Because it result in fewer impurities and little coloring, it is more preferable to employ a method for reacting (meth)acrylic anhydride with alcohol compound (D).

Compound (A) obtained above may be purified if necessary. Methods for purification are not limited specifically, and column chromatography, crystallization and the like may be employed.

In a preferred embodiment, the reaction mixture after the esterification reaction is preferred to be dissolved in a non-polar solvent, washed with an alkaline solution and/or water and then recrystallized. After recrystallization, adding a solvent with lower polarity is preferred in terms of increasing the production yield.

For example, it is preferred to use toluene as a non-polar solvent for recrystallization, and to use hexane or heptane as a solvent with lower polarity.

<(Meth)Acrylate Ester>

According to the present embodiment, in step (3), compound (A) is produced from alcohol compound (D) obtained in step (2). Thus, (meth)acrylate ester (A) with low impurity content is obtained.

More specifically, (meth)acrylate ester (A) is obtained containing a compound represented by formula (iii) at a content of less than 9 mass %, preferably 6 mass % or less.

In the present application, the content of a compound represented by formula (iii) is a ratio relative to 100 mass % of (meth)acrylate ester (A) excluding the compound represented by formula (iii).

chemical formula 24

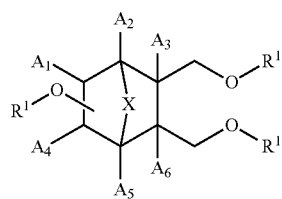

(iii)

[In the formula, $A_1$ to $A_6$ are each independently a hydrogen atom, methyl group or ethyl group, X is an oxygen atom, sulfur atom, methylene group or ethylene group, and $R^1$ is an acryloyl group or methacryloyl group.]

$A_1$ to $A_6$ and X in formula (iii) are the same as those in formula (A) including a preferred embodiment.

The amount of compound (iii) in (meth)acrylate ester (A) is measured by high-performance liquid chromatography (HPLC).

There may be isomers of compound (iii). In the present application, the amount of compound (iii) as an impurity in the (meth)acrylate ester is the total amount including those isomers.

Compound (iii) is thought to be derived from compound (ii). Therefore, when (meth)acrylate ester is produced using an alcohol compound having less compound (ii) as an impurity, (meth)acrylate ester is obtained having less compound (iii) as an impurity.

Since the compound represented by formula (iii) is a trifunctional compound, cross-linking occurs when a polymer is formed. When cross-linking occurs often, molecular weight distributions may not be as designed.

As shown in test examples later, in a polymer obtained using (meth)acrylate ester (A) as part of its monomers, the average molecular weight of the polymer increases significantly when the amount of compound (iii) relative to the amount of (meth)acrylate ester (A) is 9 mass % or greater. Namely, when the amount of compound (iii) as an impurity is less than 9 mass % relative to (meth)acrylate ester (A), impurities are less likely to affect polymer formation.

According to the present embodiment, a (meth)acrylate ester represented by formula (A') is also obtained. In (meth)acrylate ester (A') as a target product, the peak area of impurity (X), whose molecular weight is 308 and which produces methacrylic acid when decomposed during storage, is 0.3% or lower, preferably 0.2% or lower, relative to the peak area of (meth)acrylate ester (A'), based on a chromatogram obtained through high-performance liquid chromatography.

$R_1$ in formula (A') is the same as $R_1$ in formula (A).

chemical formula 25

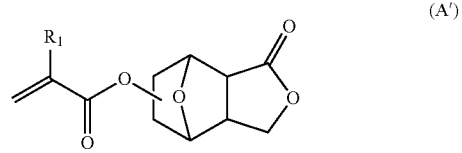

(A')

Impurity (X) above is a compound that is detected in about 16.8 minutes when measured under the HPLC conditions below.

column: Zorbax XDB-C18, 3.5 μm, 2.1 mm×150 mm (made by Agilent Technologies Inc.)

mobile phase: water/acetonitrile gradient 90/10→0/100 (30 minutes).

detector: UV detector (210 nm).

The peak area in an HPLC chromatogram correlates to the content.

"To produce methacrylic acid when decomposed during storage" means when chronological changes in the amounts of methacrylic acid and impurity (X) with a molecular weight of 308 are measured using HPLC while (meth)acrylate ester (A') is stored at a temperature range of, for example, −100° C. or higher under the decomposition temperature, preferably at a range of −20° C. to 10° C., the amount of impurity (X) decreases over time and the amount of methacrylic acid increases over time.

Impurity (X) is thought to be a compound represented by formula (Iv) below.

chemical formula 25

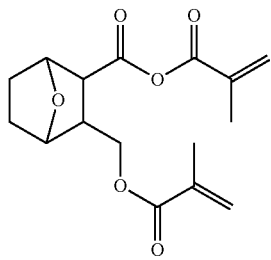

(iv)

When (meth)acrylate ester (A') containing impurity (X) is used as a monomer to form a polymer, the polymer is likely to contain methacrylic acid as an impurity. Especially, if a polymer for forming a chemically amplified resist composition contains methacrylic acid, the acid most likely causes resist performance to decrease.

By reducing the amount of impurity (X) in (meth)acrylate ester (A'), (meth)acrylate ester (A') with excellent properties is obtained.

According to the present embodiment, a (meth)acrylate ester represented by formula (A') such as follows is also obtained: the amount of methacrylic acid is at 0.04 mole ratio or lower to (meth)acrylate ester (A'); and the peak area of impurity (X), whose molecular weight is 308 and which produces methacrylic acid when decomposed during storage is 0.3% or less, preferably 0.2% or less, relative to the peak area of (meth)acrylate ester (A') in a chromatogram measured using high-performance liquid chromatography.

By reducing the amount of impurity (X) and (meth)acrylic acid in (meth)acrylate ester (A'), (meth)acrylate ester (A') with excellent properties is obtained.

According to the present embodiment, (meth)acrylate ester (A) is obtained, containing an impurity represented by formula (v) at less than 9 mass %, preferably 6 mass % or less.

In the present application, the amount of compound (v) in (meth)acrylate ester (A) is the amount in a dry powder of (meth)acrylate ester (A) with a purity degree of at least 90 mass %.

In formula (v), $A_1$ to $A_6$ are each independently a hydrogen atom, methyl group or ethyl group, X is an oxygen atom, sulfur atom, methylene group or ethylene group, and $R^2$ is a hydrogen atom, acryloyl group or methacryloyl group.]

chemical formula 27

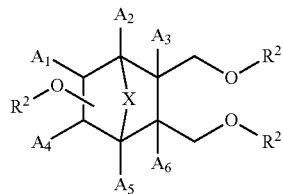

(v)

The amount of a compound represented by formula (v) is the sum of the amount of a compound represented by formula (ii) and a compound represented by formula (iii).

The amount of compound (ii) or (iii) in (meth)acrylate ester is measured using high-performance liquid chromatography (HPLC).

Compound (v) may have isomers. In the present application, the amount of compound (v) as an impurity in (meth)acrylate ester includes the amount of such isomers.

By reducing the amount of a compound represented by formula (v) in (meth)acrylate ester, (meth)acrylate ester with excellent properties is obtained.

<Polymer (P)>

Polymer (P) is described according to an embodiment of the present invention.

Polymer (P) of the present embodiment is formed by polymerizing at least one type of monomer, which includes at least one type of (meth)acrylate ester (A) or (A') containing the above-described impurity at or below a predetermined amount.

(Meth)acrylate ester (A) or (A') containing the above-described impurity at or below a predetermined amount means: (meth)acrylate ester (A) containing compound (iii) at or below a predetermined amount; (meth)acrylate ester (A') containing impurity (X) at or below a predetermined amount; (meth)acrylate ester (A') in which the total amount of impurity (X) and methacrylic acid is at or below a predetermined amount; or (meth)acrylate ester (A) containing compound (v) at or below a predetermined amount.

Polymer (P) may be a homopolymer or a copolymer. A copolymer may be a random copolymer, alternating copolymer or block copolymer.

When polymer (P) is a copolymer, it is preferred to be formed by polymerizing at least 2 types of monomers, which include at least one type of (meth)acrylate ester (A) or (A') containing the above-described impurity at or below a predetermined amount.

Polymer (P) of the present embodiment is suitable to be used for a resist composition, especially for a chemically amplified resist composition. The following are descriptions when polymer (P) is a copolymer to be used for a chemically amplified resist composition.

Resins for chemically amplified resist compositions are required to have properties such as solubility in an alkaline solution by an interaction with acid and resistance to dry etching. A polymer having a structural unit derived from (meth)acrylate ester represented by formula (A) has properties such as solubility in an alkaline solution by an interaction with acid and high resistance to dry etching, while further having excellent solubility in an organic solvent. In addition, such a polymer may include a structure having a functional group to be easily displaced by the action of acid, or a structure such as a cyclic hydrocarbon group having high resistance to dry etching.

Examples of a structure having a functional group that is easily displaced by the action of acid are, for example, a structure that protects a hydroxyl group or carboxyl group by an acetyl group, t-butyl group, tetrahydropyranyl group, methyl adamantyl group, ethyl adamantyl group or the like.

To introduce a structure having a functional group that is easily displaced by the action of acid, or a structure having high resistance to dry etching, it is an option to copolymerize a monomer having such a structure and a monomer represented by formula (A).

As for a monomer having such a structure, for example, it is an option to use a raw material monomer known as a resin for chemically amplified resist compositions. The raw material monomer in polymer (P) of the present embodiment is selected based on the light source used for lithography.

For example, when a KrF excimer laser or electron beam is the light source, polymer (P) formed by copolymerizing monomer (A) and p-hydroxystyrene or its derivative is preferred to be used considering its high resistance to etching.

In such an example, the ratio of the structural unit derived from the monomer represented by formula (A) to the entire structural unit of polymer (P) is preferred to be 1 to 50 mol %, preferably 1 to 25 mol %.

When an ArF excimer laser is the light source, polymer (P) formed by copolymerizing monomer (A) and a monomer containing a cyclic hydrocarbon group is preferred to be used. By copolymerizing a monomer having a cyclic hydrocarbon group, high light permeability and high resistance to etching are more likely to be achieved.

In such an example, the ratio of the structural unit derived from a monomer represented by formula (A) in polymer (P) is preferred to be 1 to 50 mol %, preferably 1 to 25 mol %.

Especially preferred are as follows: an acrylic copolymer formed by copolymerizing a monomer represented by formula (A), a monomer having a cyclic hydrocarbon group and a monomer having a hydrophilic functional group; an acrylic copolymer formed by copolymerizing a monomer represented by formula (1), a monomer having a cyclic hydrocarbon group and maleic anhydride; or an acrylic copolymer formed by copolymerizing a monomer represented by formula (A), a monomer having a cyclic hydrocarbon group, and a monomer having a lactone structure such as a γ-butyrolactone structure. Acrylic copolymers such as follows are known to be suitable as resins for lithography using an ArF excimer laser: an acrylic copolymer formed by copolymerizing a monomer having a cyclic hydrocarbon group and a monomer having a hydrophilic functional group; an acrylic copolymer formed by copolymerizing a monomer having a cyclic hydrocarbon group and maleic anhydride; and an acrylic copolymer formed by copolymerizing a monomer having a cyclic hydrocarbon group and a monomer having a lactone structure. By introducing a monomer unit represented by formula (A) into such a polymer, resistance to dry etching is enhanced and excellent resist patterns are obtained showing less resist surface roughness after dry etching.

A monomer unit having a cyclic hydrocarbon group provides high resistance to dry etching for a polymer containing the monomer. This is especially the case for a polymer containing a protection group (a cyclic hydrocarbon group may function directly as the protection group) that is displaced by the action of acid and provides high sensitivity as well in photolithography using an ArF excimer laser with a wavelength of 193 nm. As for a monomer unit having a cyclic hydrocarbon group, one type, or two or more types, may be selected.

Examples of a monomer unit having a cyclic hydrocarbon group are cyclohexyl (meth)acrylate, isobornyl (meth)acrylate, adamantyl (meth)acrylate, tricyclodecanyl (meth)acrylate, dicyclopentadienyl (meth)acrylate, and derivatives having a substituent such as an alkyl group,
a hydroxyl group or a carboxyl group on the cyclic hydrocarbon group in the monomers above.

A monomer unit having a hydrophilic functional group provides a polymer with adhesiveness to a substrate. Especially, a monomer unit having a protection group that will be displaced by the action of acid provides high sensitivity in photolithography using an ArF excimer laser with a wavelength of 193 nm. Examples of a hydrophilic functional group are a carboxylic group, hydroxyl group, cyano group, methoxy group, amino group, alkyl-substituted ether group (alkyl-substituted ether group having 4 or fewer carbon atoms), δ-valero lactonitrile group, and γ-butyro lactonitrile group. Among the above, some are categorized as hydrophobic, but as long as they have hydrophilic properties necessary in the lithographic process, such monomers are also listed above. One type or two or more types of monomer units with a hydrophilic group may be used depending on requirements.

Examples of a monomer unit having a hydrophilic functional group are (meth)acrylic acid, (meth)acrylate with a terminal hydroxyl group, (meth)acrylate with an alkyl-substituted ether group, (meth)acrylate with a δ-valero lactonile group, (meth)acrylate with a γ-butyro lactonile group, and derivatives having a substituent such as an alkyl group, hydroxyl group, carboxyl group and cyano group on a hydrophilic functional group of the above monomers excluding (meth)acrylic acid.

A monomer unit with a lactone structure provides a polymer that contains such a monomer unit with high resistance to dry etching and adhesiveness to a substrate. The monomer unit having a lactone structure may be used alone or two or more may be combined thereof.

As for a monomer unit having a lactone structure, they include α-methylene lactones with 4- to 8-member rings and their derivatives having a substituent such as an alkyl group, hydroxyl group or carboxyl group on such a latone ring.

As a resin for a chemically amplified resist composition, an acrylic copolymer formed as follows is preferred: 1 to 60 mol % of a structural unit derived from compound (A); 1 to 60 mol % of a structural unit derived from a monomer having a cyclic hydrocarbon group; 1 to 60 mol % of a structural unit derived from a monomer having a hydrophilic functional group; and 1 to 60 mol % of a structural unit having a lactone structure.

The weight-average molecular weight of polymer (P) used as a resin for chemically amplified resist composition is not limited specifically, but 1000 to 100000 is preferred, and 3000 to 30000 is more preferable. The greater the weight-average molecular weight, the better the resist shape is likely to be because the resistance to dry etching is improved. Also, the smaller the weight-average molecular weight, the better the resolution is likely to be because solubility to the resist solution is improved.

<Method for Producing Polymer (P)>

Polymer (P) of the present embodiment is produced using well-known polymerization methods. However, when simplified production is considered, it is preferred to employ so-called dropping polymerization methods such as dropping a monomer solution, which is prepared in advance by dissolving a monomer and a polymerization initiator in an organic solvent, into an organic solvent retained at a constant temperature.

Organic solvents used in dropping polymerization methods are not limited specifically. However, solvents capable of dissolving both monomers and a resultant copolymer are preferred. For example, 1,4-dioxane, isopropyl alcohol, acetone, tetrahydrofuran, ethyl lactate and the like are listed. The amount of such a solvent is not limited specifically, and is determined properly.

A polymerization initiator for dropping polymerization is not limited specifically. Examples are azo compounds such as azobisisobutyronitrile and 2,2'-azobis(2,4-dimethyl)valeronitrile), and organic peroxides such as benzoyl peroxide. Also, mercaptans such as n-butyl mercaptan and n-octyl mercaptan may also be used as a chain-transfer agent. The amount of a polymerization initiator or chain-transfer agent is not limited specifically, and is determined properly.

Polymerization temperature during dropping polymerization is not limited specifically. Usually, it is preferred to be set in a range of 50 to 150° C. The dropping duration is not limited specifically, but it is preferred to be set for six hours or longer. Also, after dropping is finished, the dropping temperature is preferred to be retained for about 1 to 3 hours so that polymerization will be completed.

The polymerization solution produced by dropping polymerization is diluted using a good solvent such as tetrahydrofuran and 1,4-dioxane to have a proper viscosity, and is dropped in a large-amount poor solvent such as heptane, methanol or water so that a polymer is precipitated. Then, the precipitation is filtered and dried thoroughly to obtain polymer (P) of the present embodiment.

The step for dropping a polymer solution into a large-amount poor solvent to precipitate a polymer is called resedimentation. It is very effective to remove unreacted monomers, polymerization initiator or the like remaining in the polymer solution. Since such remaining unreacted monomers and the like may cause a negative effect on the resist performance, it is preferred to remove them. Such a resedimentation process may be optional.

<Resist Composition>

An embodiment of resist compositions is described.

The resist composition of the present embodiment is a chemically amplified resist composition containing polymer (P) (resin for chemically amplified resist compositions of the above embodiment) and a compound that generates an acid when irradiated by active light or radiation. Polymer (P) may be used alone, or two or more may be combined.

The amount of polymer (P) to the resist composition (excluding solvents) is not limited specifically, but 70 to 99.8 mass % is preferred.

The photoacid generator used in the resist composition of the present embodiment is selected freely among those usable as acid generators in resist compositions. A photoacid generator may be used singularly, or two or more types may be combined.

Examples of a photoacid generator are onium salt compounds, sulfone imide compounds, sulfone compounds, sulfonate esters compounds, quinone diazide compounds, diazomethane compounds and the like. Among them, onium salt compounds such as sulfonium salts, iodonium salts, phosphonium salts, diazonium salts and pyridinium salts are preferred.

The amount of a photoacid generator is determined properly depending on the type of photoacid generator or the like. Usually, it is preferred to use 0.1 to 20 parts by mass, more preferably 0.5 to 10 parts by mass, to 100 parts by mass of polymer (P). When the amount of a photoacid generator is at least the lower limit in the above range, it is easier to start the chemical reaction catalyzed by the acid generated through exposure to light. In addition, if the amount is no greater than the upper limit of the above range, stability of the resist composition is enhanced, and uneven coating when the composition is applied or scum or the like during development is sufficiently suppressed.

A solvent used for the resist composition of the present embodiment is selected properly according to usage purposes. In addition to the solubility of resin, selection of solvents may face limitations such as uniformity of coated film, exterior, safety and the like.

Examples of solvents usually used in the present embodiment are as follows: linear ketones such as 2-pentanone and 2-hexanone; cyclic ketones such as cyclopentanone and cyclohexanone; propylene glycol monoalkyl acetates such as propylene glycol monomethyl ether acetate and propylene glycol monoethyl ether acetate; ethylene glycol monoalkyl ether acetates such as ethylene glycol monomethyl ether acetate and ethylene glycol monoethyl ether acetate; propylene glycol monoalkyl ethers such as propylene glycol monomethyl ether and propylene glycol monoethyl ether; ethylene glycol monoalkyl ethers such as ethylene glycol monomethyl ether and ethylene glycol monoethyl ether; diethylene glycol alkyl ethers such as diethylene glycol dimethyl ether and diethylene glycol diethyl ether; esters such as ethyl acetate and ethyl lactate; alcohols such as cyclohexanol and 1-octanol; ethylene carbonate and γ-butyrolactone. Those solvents may be used alone, or two or more may be combined.

The amount of solvents depends on the thickness of resist film to be formed. Usually, 100 to 10000 parts by mass to 100 parts by mass of polymer (P) (resist polymer) is preferred.

Moreover, the resist composition of the present embodiment may contain various well-known additives such as surfactants, quenchers, sensitizers, halation inhibitors, preservation stabilizers, antifoaming agents and the like, if necessary. The amounts of such additives are not limited specifically, and may be determined appropriately.

<Method for Producing Substrate with Patterns>

A method for producing a substrate with patterns formed thereon is described according to an embodiment of the present invention.

The method for producing a substrate with patterns formed thereon according to the present embodiment includes a step in which the resist composition of the above embodiment is applied onto a surface of a substrate to form a resist film, a step in which the resist film is exposed to light, and a step in which the exposed resist film is developed using a developing solution.

More specifically, first, the resist composition is applied by spin coating or the like onto a surface of a substrate to be processed such as a silicon wafer to form patterns. Next, the substrate with applied resist composition is dried by baking treatment (prebake) or the like so that a resist film is formed on the substrate.

Next, the resist film is irradiated by light with a wavelength of 250 nm or shorter through a photomask (exposure to light). For exposure to light, light with a wavelength of 220 nm or shorter, especially ArF excimer laser, is preferred.

A post-exposure bake (PEB) is conducted after irradiation of light (exposure to light), and the substrate is immersed in an alkaline developing solution so that the exposed portions of the resist film are dissolved in the developing solution to be removed (development). Any well-known alkaline developing solution may be used. Then, rinsing treatment is conducted on the substrate using pure water or the like. Accordingly, resist patterns are formed on the substrate.

Then, baking treatment on the substrate with resist patterns is conducted (post bake) to strengthen the resist, and portions without the resist are selectively etched. After the etching process, the resist is usually removed using a remover.

<Novel Compound>

A compound represented by formula (iii) is a novel compound.

In formula (iii), $A_1$ to $A_6$ are each independently a hydrogen atom, methyl group or ethyl group. A hydrogen atom or a methyl group is preferred. The total number of methyl and ethyl groups in one molecule is any number of 0 to 6, but 0 to 2 is preferred, more preferably 0 to 1, when the compound is used as a monomer for a resist resin.

X is an oxygen atom, sulfur atom, methylene group or ethylene group. Among those, an oxygen atom or a methylene group is preferred. $R^1$ is an acryloyl group or methacryloyl group.

Among the compounds represented by formula (iii), a compound represented by formula (iii') is especially preferred. In the formula, $R^1$ is an acryloyl group or methacryloyl group.

chemical formula 28

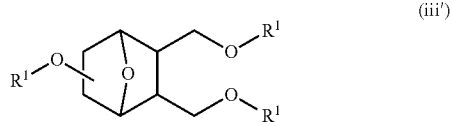

(iii')

A compound represented by formula (iii) is produced by generating a compound (triol compound) represented by formula (ii) from acid anhydride (B) through reduction reactions, which is then esterified.

The same reduction agent as used in method (II) for producing a lactone compound or step (1) (reduction process) may be used here. Sodium borohydride is preferred in terms of reactivity.

The amount of a reduction agent is 1 to 30 mol, preferably 3 to 10 mol, per 1 mol of acid anhydride (B). If the amount of a reduction agent is more than the upper limit of the above range, the yield of desired product decreases, and if the amount is less than the lower limit, a process after reactions becomes complex.

The solvent used for reduction reactions is the same as used in method (II) for producing a lactone compound or step (1) (reduction process) above. In terms of solubility of the raw material, a mixed solvent of tetrahydrofuran and methanol, or a mixed solvent of dimethoxyethane and alcohols.

During reduction reactions, the reaction temperature is preferred to be −50 to 100° C., more preferably −30 to 30° C.

After reduction reactions have progressed thoroughly, acid is added for neutralization. To extract compound (ii) from the reaction solution, extraction, crystallization, distillation, column purification or the like may be employed.

Next, compound (ii) is esterified to obtain compound (iii). Well-known esterification reaction methods are employed, the same as in step (3) above (esterification process) such as reacting (meth)acrylic acid halide or (meth)acrylic anhydride with compound (iii) in the presence of a base.

<Polymer (Q)>

Polymer (Q) formed by using compound (iii) as a monomer is described according to an embodiment of the present invention.

Polymer (Q) of the present embodiment is formed by polymerizing at least one type of monomer. At least one type of the monomers is compound (iii).

Polymer (Q) may be a homopolymer or a copolymer. Such copolymers may be a random copolymer, alternating copolymer, or block copolymer.

When it is a copolymer, it is preferred that such a polymer be formed by polymerizing at least two types of monomers, including compound (iii) and a (meth)acrylate ester other than compound (iii).

A (meth)acrylate ester to be copolymerized with compound (iii) is not limited specifically, and may be selected properly according to usage purposes or the like.

The monomer unit derived from compound (iii) is preferred to be 1 to 100 mol %, more preferably 3 to 100 mol %, even more preferably 5 to 100 mol % to the entire structural unit of polymer (Q).

<Method for Producing Polymer (Q)>

Polymer (Q) of the present embodiment is produced by using a well-known polymerization method. The same method as for polymer (P) may be employed.

Polymer (Q) having a structural unit derived from compound (iii) has excellent properties such as curability, water resistance, flexibility and alkali resistance. Moreover, since the ether bond is positioned on the outer side of the polymer chain because of its unique conformation, adhesiveness to a substrate is enhanced. Using such a structure, the ratio of isomers to the polymer is controlled, and the stereoregularity of the polymer is controlled accordingly.

EXAMPLES

In the following, examples of the present invention are described in detail. However, the present invention is not limited to such examples. Unless otherwise indicated in the examples, commercially available monomers and reaction agents are used without purifying them.

The pH values were measured by a pH meter (SevenEasy-KS, made by Mettler Toledo International Inc.)

Production Example of Acid Anhydride (B)

Synthesis Example (B1)

chemical formula 29

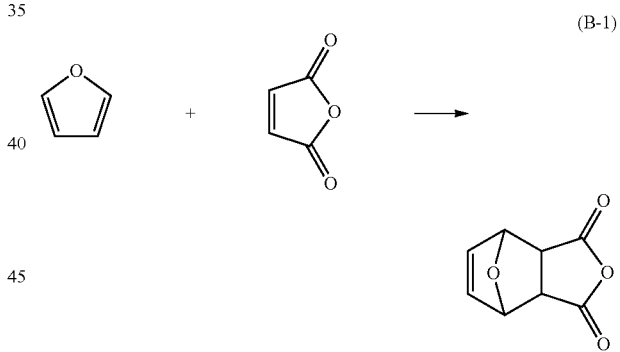

(B-1)

In a flask with attached dropping funnel, thermometer, calcium chloride tube and stirrer, maleic anhydride (98.06 grams, 1 mmol) and toluene (400 mL) were added and the stirring was started. After furan (68.07 grams, 1 mmol) was dropped at 20° C., the mixture was stirred at 20° C. for 16 hours. After the reactions were completed, the deposited crystals were suction-filtered and acid anhydride (B-1) (128.58 grams, 77.4% yield) was obtained.

{Method for Producing Lactone Compound (C)}

The measurement method was as follows.

(Measurement by HPLC)

Through HPLC under conditions below, concentrations were measured for 4-oxatricyclo[5.2.1.0$^{2,6}$]decene-3-one as the target product, 5-norbornene-2,3-carboxylic anhydride as a raw material, and (3-hydroxymethyl-bicyclo[2.2.1]-hept-5-en-2-yl)-methanol as a byproduct.

column: INERTSIL ODS-3V (4.64ϕ×250 mm), made by GL Sciences, Inc.

mobile phase: an eluent prepared by mixing a 0.1 mass % phosphoric acid solution and acetonitrile at a mass ratio of 50:50.

flow rate: 1.0 mL/min.

detector: differential refractive index detector (RI detector)

column temperature: 40° C.

Through HPLC under conditions below, concentrations were measured for 4,10-dioxatricyclo[5.2.1.0$^{2,6}$]deca-8-en-3,5-dione as a raw material, 4,10-dioxatricyclo[5.2.1.0$^{2,6}$]deca-8-en-3-one as the target product, and (3-hydroxymethyl-7-oxabicyclo[2.2.1]-hept-5-en-2-yl)-methanol as a byproduct.

column: YMC-Pack Pro C18 (4.6φ×150 mm).

mobile phase: an eluent prepared by mixing a 0.1 mass % phosphoric acid solution and MeOH at a mass ratio of 95:5.

flow rate: 0.5 mL/min.

detector: differential refractive index detector (RI detector)

column temperature: 40° C.

The concentration of 5-norbornene-2,3-carboxylic anhydride was obtained by the formula below:

(the area of 5-norbornene-2,3-carboxylic anhydride)/
(the area of 5-norbornene-2,3-carboxylic anhydride+the area of 4-oxatricyclo[5.2.1.0$^{2,6}$]decene-3-one+the area of (3-hydroxymethyl-bicyclo[2.2.1]-hept-5-en-2-yl)-methanol)×100.

The concentration of 4-oxatricyclo[5.2.1.0$^{2,6}$]decene-3-one was obtained by the formula below:

(the area of 4-oxatricyclo[5.2.1.0$^{2,6}$]decene-3-one)/
(the area of 5-norbornene-2,3-carboxylic anhydride+the area of 4-oxatricyclo[5.2.1.0$^{2,6}$]decene-3-one+the area of (3-hydroxymethyl-bicyclo[2.2.1]-hept-5-en-2-yl)-methanol)×100.

The concentration of (3-hydroxymethyl-bicyclo[2.2.1]-hept-5-en-2-yl)-methanol was obtained by the formula below:

((the area of (3-hydroxymethyl-bicyclo[2.2.1]-hept-5-en-2-yl)-methanol)/(the area of 5-norbornene-2,3-carboxylic anhydride+the area of 4-oxatricyclo[5.2.1.0$^{2,6}$]decene-3-one+the area of (3-hydroxymethyl-bicyclo[2.2.1]-hept-5-en-2-yl)-methanol)×100.

The concentration of 4,10-dioxatricyclo[5.2.1.0$^{2,6}$]deca-8-en-3,5-dione was obtained by the formula below:

(the area of 4,10-dioxatricyclo[5.2.1.0$^{2,6}$]deca-8-en-3,5-dione)/(the area of 4,10-dioxatricyclo-[5.2.1.0$^{2,6}$]deca-8-en-3,5-dione+the area of 4,10-dioxatricyclo[5.2.1.0$^{2,6}$]deca-8-en-3-one+the area of (3-hydroxymethyl-7-oxabicyclo[2.2.1]-hept-5-en-2-yl)-methanol)×100.

The concentration of 4,10-dioxatricyclo[5.2.1.0$^{2,6}$]deca-8-en-3-one was obtained by the formula below:

(the area of 4,10-dioxatricyclo[5.2.1.0$^{2,6}$]deca-8-en-3-one)/(the area of 4,10-dioxatricyclo[5.2.1.0$^{2,6}$]deca-8-en-3,5-dione+the area of 4,10-dioxatricyclo[5.2.1.0$^{2,6}$]deca-8-en-3-one+the area of (3-hydroxymethyl-7-oxabicyclo[2.2.1]-hept-5-en-2-yl)-methanol)×100.

The concentration of (3-hydroxymethyl-7-oxabicyclo[2.2.1]-hept-5-en-2-yl)-methanol was obtained by the formula below:

(the area of (3-hydroxymethyl-7-oxabicyclo[2.2.1]-hept-5-en-2-yl)-methanol)/(the area of 4,10-dioxatricyclo[5.2.1.0$^{2,6}$]deca-8-en-3,5-dione+the area of 4,10-dioxatricyclo[5.2.1.0$^{2,6}$]deca-8-en-3-one+the area of (3-hydroxymethyl-7-oxabicyclo[2.2.1]-hept-5-en-2-yl)-methanol)×100.

($^1$H-NMR Measurement)

Using a superconducting FT-NMR (model JNM-GX 270, made by JEOL Ltd.), $^1$H-NMR was measured by integrating $^1$H 32 times under conditions below:

An approximately 5 mass % solution (deuterated chloroform solution) of (3-hydroxymethyl-bicyclo[2.2.1]-hept-5-en-2-yl)-methanol or a solution (deuterated chloroform solution) of (3-hydroxymethyl-7-oxabicyclo[2.2.1]-hept-5-en-2-yl)-methanol is put in a sample tube with a diameter of 5 mm; and the observation frequency was set at 270 MHz in single pulse mode. An ampoule bottle of deuterated chloroform solution was opened shortly before the preparation of samples to be used as a solvent. The measurement temperature was set at 20° C.

Example C1

A magnetic stirrer was placed in a 50 mL three-neck round-bottom flask (reactor) with a dropping funnel having a 50 mL side tube, a thermometer and a reflux condenser and was heated and dried in a flow of nitrogen gas. Then, 2.07 grams of tetrahydrofuran (hereinafter referred to as THF) and 0.62 grams (0.016 mol) of sodium borohydride were put into the flask in that order. In the dropping funnel, 3.00 grams (0.018 mol) of 5-norbornene-2,3-dicarboxylic anhydride (a compound represented by formula (4), where $R^{11}$ to $R^{16}$ are each a hydrogen atom, and X is a methylene group), 9.68 grams of THF, and 0.59 grams (0.061 mol) of methanol were placed and dissolved. Next, the reactor was cooled in an ice bath to 5° C., and the stock solution was dropped out in 15 minutes from the dropping funnel while the solution was stirred. During that time, the temperature of the reaction mixture was kept at 10 to 15° C.

After the completion of dropping, stirring the reaction mixture continued while its temperature was kept at 13 to 17° C. Then, 30 minutes, 90 minutes and 150 minutes respectively after the completion time, 0.2 mL each of the reaction mixture was divided into a 10 mL measuring flask. The mass of each divided reaction mixture was measured, and 0.2 mL of a 30 mass % sulfuric acid solution was added into each measuring flask and stirred well. Then, the mobile phase of HPLC was added to fill up to 10 mL, stirred well and analyzed by HPLC. The results are shown in Table 1.

Example C2

Reaction procedures and post-processing procedures were conducted the same as in Example C1 except that 1.83 grams of THF and 0.55 grams (0.015 mol) of sodium borohydride were put into the three-neck round-bottom flask (reactor). The results are shown in Table 1.

Example C3

Reaction procedures and post-processing procedures were conducted the same as in Example C1 except that 2.19 grams of THF and 0.65 grams (0.017 mol) of sodium borohydride were put into the three-neck round-bottom flask (reactor). The results are shown in Table 1.

Comparative Example C1

Reaction procedures and post-processing procedures were conducted the same as in Example C1 except that 1.60 grams of THF and 0.48 grams (0.013 mol) of sodium borohydride were put into the three-neck round-bottom flask (reactor). The results are shown in Table 1.

Comparative Example C2

Reaction procedures and post-processing procedures were conducted the same as in Example C1 except that 2.30 grams of THF and 0.69 grams (0.018 mol) sodium borohydride were put into the three-neck round-bottom flask (reactor), The results are shown in Table 1.

Example C4

Reaction procedures and post-processing procedures were conducted the same as in Example C1 except for the following: 0.70 grams (0.018 mol) of sodium borohydride and 6.97 grams of DME instead of THF were put into the three-neck round-bottom flask (reactor); and in the dropping funnel, 5-norbornene-2,3-dicarboxylic anhydride was replaced with, 3.40 grams (0.020 mol) of 4,10-dioxatricyclo[5.2.1.0$^{2,6}$]deca-8-en-3,5-dione (a compound represented by formula (4), where $R^{11}$ to $R^{16}$ are each a hydrogen atom, and X is an oxygen atom; acid anhydride (B-1) produced in synthesizing example B1 was used), 9.68 grams of THF was replaced with 39.10 grams of DME, and the amount of methanol was changed from 0.59 grams (0.061 mol) to 0.66 grams (0.020 mol). The results are shown in Table 2.

Example C5

Reaction procedures and post-processing procedures were conducted the same as in Example C4 except that 6.19 grams of DME and 0.62 grams (0.016 mol) of sodium borohydride were put into the three-neck round-bottom flask (reactor). The results are shown in Table 2.

Comparative Example C3

Reaction procedures and post-processing procedures were conducted the same as in Example C4 except that 4.65 grams of DME and 0.46 grams (0.012 mol) of sodium borohydride were put into the three-neck round-bottom flask (reactor). The results are shown in Table 2.

Comparative Example C4

Reaction procedures and post-processing procedures were conducted the same as in Example C4 except that 7.74 grams of DME and 0.77 grams (0.020 mol) of sodium borohydride were put into the three-neck round-bottom flask (reactor). The results are shown in Table 2.

Reference Example C1

Identification of (3-hydroxymethyl-bicyclo[2.2.1]-hept-5-en-2-yl)-methanol

Into the reaction mixture obtained in comparative example C1, 6.0 grams (0.018 mol) of a 30 mass % sulfuric acid solution was dropped out in 60 minutes while keeping the temperature at 10 to 20° C. After the dropping was completed, the reaction mixture was retained at 20° C. for 1 hour, and 12 grams of toluene was added to conduct extraction three times. The toluene phase was washed once with 4 grams of a saturated sodium bicarbonate solution, and washed one more time with 4 grams of water. The obtained toluene phase was concentrated under reduced pressure, and purified through column chromatography. Accordingly, 0.04 grams of (3-hydroxymethyl-bicyclo[2.2.1]-hept-5-en-2-yl)-methanol was obtained.

Results of the $^1$H-NMR measurements of (3-hydroxymethyl-bicyclo[2.2.1]-hept-5-en-2-yl)-methanol were as follows: 1.3 to 1.4 ppm 2H(C7-H2), 2.5 to 2.6 ppm 2H(C2-H, C3-H), 2.8 ppm 2H(C1-H, C4-H), 3.3 to 3.7 ppm 6H(OH, —O—C—H2), and 6.0 ppm 2H(C5-H, C6-H).

Reference Example C2

Identification of (3-hydroxymethyl-7-oxabicyclo[2.2.1]-hept-5-en-2-yl)-methanol

The same procedures were conducted as in reference example C1 except that the reaction mixture obtained in comparative example C2 was used to obtain 0.05 grams of (3-hydroxymethyl-7-oxa bicyclo[2.2.1]-hept-5-en-2-yl)-methanol.

Results of the $^1$H-NMR measurements of (3-hydroxymethyl-7-oxa bicyclo[2.2.1]-hept-5-en-2-yl)-methanol were as follows: 1.9 to 2.0 ppm 2H(C2-H, C3-H), 3.5 to 3.6 ppm 2H(OH), 3.7 to 3.9 ppm 4H (—O—C—H2), 4.6 to 4.7 ppm 2H(C1-H, C4-H), and 6.4 ppm 2H(C5-H, C6-H).

TABLE 1

| | amount of sodium borohydride (to 5-norbornene-2,3-carboxylic anhydride) | compound in the system | 30 min | 90 min | 150 min | reaction yield |
|---|---|---|---|---|---|---|
| example C1 | 0.9 mole ratio | 4-oxatricyclo[5.2.1.0$^{2,6}$]decene-3-one | 98% | 97% | 96% | 88% |
| | | 5-norbornene-2,3-carboxylic anhydride | 2% | 2% | 2% | |
| | | (3-hydroxymethyl-bicyclo[2.2.1]-hept-en-2-yl)-methanol | 0% | 1% | 2% | |
| example C2 | 0.8 mole ratio | 4-oxatricyclo[5.2.1.0$^{2,6}$]decene-3-one | 94% | 98% | 98% | 87% |
| | | 5-norbornene-2,3-carboxylic anhydride | 6% | 2% | 2% | |
| | | (3-hydroxymethyl-bicyclo[2.2.1]-hept-en-2-yl)-methanol | 0% | 0% | 0% | |
| example C3 | 0.95 mole ratio | 4-oxatricyclo[5.2.1.0$^{2,6}$]decene-3-one | 98% | 97% | 96% | 87% |
| | | 5-norbornene-2,3-carboxylic anhydride | 2% | 2% | 2% | |
| | | (3-hydroxymethyl-bicyclo[2.2.1]-hept-en-2-yl)-methanol | 0% | 1% | 2% | |
| comparative example C1 | 0.6 mole ratio | 4-oxatricyclo[5.2.1.0$^{2,6}$]decene-3-one | 77% | 77% | 77% | 57% |
| | | 5-norbornene-2,3-carboxylic anhydride | 23% | 23% | 23% | |
| | | (3-hydroxymethyl-bicyclo[2.2.1]-hept-en-2-yl)-methanol | 0% | 0% | 0% | |
| comparative example C2 | 1.0 mole ratio | 4-oxatricyclo[5.2.1.0$^{2,6}$]decene-3-one | 97% | 96% | 95% | 81% |
| | | 5-norbornene-2,3-carboxylic anhydride | 2% | 2% | 2% | |
| | | (3-hydroxymethyl-bicyclo[2.2.1]-hept-en-2-yl)-methanol | 1% | 2% | 3% | |

TABLE 2

| | amount of sodium borohydride (to 4,10-dioxatricyclo[5.2.1.0$^{2,6}$]deca-8-en-3-one) | compound in the system | 30 min | 90 min | 150 min | reaction yield |
|---|---|---|---|---|---|---|
| example C4 | 0.9 mole ratio | 4,10-dioxatricyclo[5.2.1.0$^{2,6}$]deca-8-en-3-one | 97% | 97% | 96% | 95% |
| | | 4,10-dioxatricyclo[5.2.1.0$^{2,6}$]deca-8-en-3,5-dione | 2% | 2% | 2% | |
| | | (3-hydroxymethyl-7-oxabicyclo[2.2.1]-hept-en-2-yl)-methanol | 1% | 1% | 2% | |
| example C5 | 0.8 mole ratio | 4,10-dioxatricyclo[5.2.1.0$^{2,6}$]deca-8-en-3-one | 99% | 99% | 98% | 92% |
| | | 4,10-dioxatricyclo[5.2.1.0$^{2,6}$]deca-8-en-3,5-dione | 1% | 1% | 1% | |
| | | (3-hydroxymethyl-7-oxabicyclo[2.2.1]-hept-en-2-yl)-methanol | 0% | 0% | 1% | |
| comparative example C3 | 0.6 mole ratio | 4,10-dioxatricyclo[5.2.1.0$^{2,6}$]deca-8-en-3-one | 78% | 80% | 82% | 70% |
| | | 4,10-dioxatricyclo[5.2.1.0$^{2,6}$]deca-8-en-3,5-dione | 22% | 20% | 18% | |
| | | (3-hydroxymethyl-7-oxabicyclo[2.2.1]-hept-en-2-yl)-methanol | 0% | 0% | 0% | |
| comparative example C4 | 1.0 mole ratio | 4,10-dioxatricyclo[5.2.1.0$^{2,6}$]deca-8-en-3-one | 98% | 97% | 96% | 90% |
| | | 4,10-dioxatricyclo[5.2.1.0$^{2,6}$]deca-8-en-3,5-dione | 1% | 1% | 1% | |
| | | (3-hydroxymethyl-7-oxabicyclo[2.2.1]-hept-en-2-yl)-methanol | 1% | 2% | 3% | |

As shown in Tables 1 and 2, when the amount of sodium borohydride was 0.7 to 0.95 mole ratio (examples C1 to C5) relative to the compound represented by formula (1) above during reduction reactions, it was confirmed that dialcohol byproducts measured 30 minutes after the reaction completion were suppressed to be less than 1 mass % and high reaction yields were achieved. By contrast, when the amount of sodium borohydride was 1.0 mole ratio (comparative examples C2, C4) relative to the compound represented by formula (1) above, it was confirmed that dialcohol byproducts measured 30 minutes after the reaction completion could not be suppressed to be less than 1 mass %. In addition, when the amount of sodium borohydride was 0.6 mole ratio (comparative examples C1, C3) relative to the compound represented by formula (1) above, it was confirmed that dialcohol byproducts measured 30 minutes after the completion of the reaction were suppressed to be less than 1 mass %, but that reaction yields were low.

Production Example of Alcohol Compound (D)

In the example below, lactone compound (C-1) is a compound (4,10-dioxatricyclo[5.2.1.0$^{2,6}$]deca-8-en-3-one) represented by formula (C-1) produced in the same manner as in example C4 above.

Example D1

In a flask with attached thermometer, calcium chloride tube and stirrer and nitrogen inlet tube, 1.5 grams (0.01 mol) of lactone compound (C-1) and 18 grams of dimethoxyethane were placed and stirred at room temperature for 30 minutes to form a lactone solution. Then, the solution was cooled to 20° C. Into the lactone solution, 0.56 grams of BH$_3$.dimethyl sulfide complex was dropped at such a rate that the lactone solution temperature was kept at 20 to 23° C. After the dropping was completed, the obtained mixture was stirred at 20° C. for 1.5 hours. Those procedures were conducted under nitrogen current.

To the mixture, 7.9 grams of a 5 mass % NaOH solution was added, and 1.2 mL of hydrogen peroxide (30 mass % solution) was slowly added. Next, the mixture was stirred for 2 hours while its temperature was kept at 30° C. Then, while cooling the mixture, 50 mass % sulfuric acid was dropped into the reaction mixture to a pH of 1 (pH at 30° C.), and further stirred at 30° C. for one hour. While further cooling, a 28 mass % ammonia solution was dropped to neutralize the mixture to be a pH of 6.5 (pH at 20° C.), the mixture was filtered and the filtrate was washed with dimethoxyethane.

When the filtrate was analyzed through liquid chromatography (HPLC) under conditions below, the area percentages of the components except for the solvent were: a compound represented by formula (C-1) at 0%, a compound represented by formula (D-1) at 75%, a compound represented by formula (ii-1) at 1%, and a compound represented by formula (i-1) at 0%. In addition to those, peaks of sulfates and borates were also detected.

chemical formulas 30

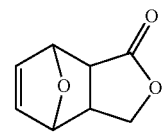

(C-1)

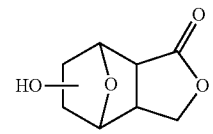

(D-1)

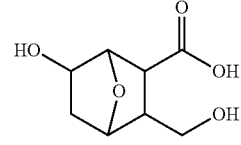

(i-1)

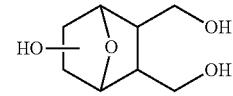

(ii-1)

(HPLC Conditions)
column: INERTSIL ODS-3V (4.6φ×250 mm), made by GL Sciences, Inc.
mobile phase: a 0.1 mass % phosphoric acid solution/acetonitrile gradient: 100/0 (5 minutes), 100/0→10/90 (25 minutes)
flow rate: 1.0 mL/min.
detector: UV detector
column temperature: 40° C.
The filtrate was concentrated by evaporator, and 30 grams of ethanol was added, and the solution was concentrated again. After such procedure was repeated twice, the concentration was dissolved in 30 grams of ethanol and filtered. The filtrate was concentrated until the entire amount reached 4.1 grams, and was dissolved at 70° C. The mixture was cooled to 20° C. at a programmed rate of 20° C./hr, and 6.3 grams of diisopropyl ether was dropped into the mixture, which was then retained at 3° C. for 15 minutes and filtered again. The filtrate was washed with diisopropyl ether.

Such procedures were conducted while the mixture was stirred.

The weight of the dry filtrate (dried product of the alcohol compound) was 1.3 grams, and it contains a compound represented by formula (D-1) at 99% in area percentage, and no compound represented by formula (C-1) or (ii-1) was detected.

Example D2

In a flask with attached thermometer, calcium chloride tube, stirrer and nitrogen inlet tube, 1.8 grams (0.012 mol) of lactone compound (C-1) and 15 mL of tetrahydrofuran were placed and stirred at room temperature for 30 minutes to form a lactone solution. Then, the solution was cooled to 0° C. Into the lactone solution, 4 mL of 1M BH$_3$.tetrahydrofuran complex was dropped at such a rate that the lactone solution temperature was kept at 0° C. After the dropping was completed, the obtained mixture was stirred for 3 minutes at 0° C. and for 4 hours at room temperature. Those procedures were conducted under nitrogen current.

To the mixture, 4 mL of a 3N NaOH solution was added, and 4 mL of hydrogen peroxide (30 mass % solution) was slowly added. Next, the mixture was stirred for 1.5 hours at 50° C. Then, 50 mass % sulfuric acid was dropped into the reaction mixture to a pH of 1 (pH at 30° C.), and further stirred at 30° C. for an hour.

When the reaction mixture was analyzed through HPLC under conditions the same as in example D1, the area percentages of the components except for the solvent were:

a compound represented by formula (C-1) at 4%, a compound represented by formula (D-1) at 95%, a compound represented by formula (ii-1) at 1%, and a compound represented by formula (i-1) at 0%. Peaks of sulfates and borates were not detected since those peaks overlapped with negative peaks of the solvent.

A 28 mass % of ammonia solution was dropped into the reaction mixture while the mixture was cooled to be neutralized to a pH of 6.5 (pH at 30° C.). Then, the mixture was filtered and the filtrate was washed with dimethoxyethane.

After the filtrate was concentrated by an evaporator and 30 grams of ethanol was added, the mixture was further concentrated. Such procedures were repeated twice, and the concentrated mixture was dissolved in 30 grams of ethanol and filtered. The mixture was concentrated until the entire amount reached 4.1 grams, and was dissolved at 70° C. The mixture was cooled to 20° C. at a programmed rate of 20° C./hr, and 6.3 grams of diisopropyl ether was dropped into the mixture, which was then retained at 3° C. for 15 minutes, and filtered again. The filtrate was washed with diisopropyl ether.

Such procedures were conducted while the mixture was stirred.

The weight of the dry filtrate was 1.3 grams and it contained a compound represented by formula (D-1) at 96% and a compound represented by formula (C-1) at 4% in area percentage, but no compound represented by (ii-1) was detected.

Comparative Example D1

Steps for reacting a compound represented by formula (C-1) and BH$_3$.tetrahydrofuran complex, for adding an NaOH solution and hydrogen peroxide, and for stirring at 50° C. for 1.5 hours are conducted the same as in example D2, and the obtained reaction mixture was analyzed through liquid chromatography. Acid was not added to the reaction mixture.

As a result, the area percentages were: a compound represented by formula (C-1) at 3%, a compound represented by formula (D-1) at 34%, a compound represented by formula (ii-1) at 1%, and a compound represented by formula (i-1) at 38%. Peaks of sulfates and borates were not detected since those peaks overlapped with the negative peaks of the solvent.

Namely, the amount of a target compound represented by formula (D-1) was almost the same as a byproduct compound represented by formula (i-1).

When the reaction mixture was saturated with potassium carbonate, two layers were observed. The two layers were separated and the aqueous layer was extracted with THF. The obtained THF solution was washed with saturated NaCl, and the solvent was removed under reduced pressure to cause a white semi-solid product. Such a white solid was purified through chromatography, but the target compound (compound (D-1)) was not collected (a solution of 95 mass % of methylene chloride and 5 mass % of methanol was used).

Production Method for (Meth)acrylate Ester (A)

Example A1

<1-1 Reduction Process>

In a flask with attached dropping funnel, thermometer, calcium chloride tube and stirrer, sodium borohydride (3.43 grams, 90.7 mmol) and DMAc (3.43 mL) were added, and cooled to 5° C. Meanwhile, acid anhydride (B-1) synthesized in synthesis example B1 (25.11 grams, 151.1 mmol) was dissolved in DMAc (100 mL) and dropped out from the dropping funnel in an hour. During that time, the temperature of the mixture in the flask was 15° C. or lower. Reactions progressed at 20° C. for 4 hours, and the mixture was cooled to 5° C. Then, a solution of sulfuric acid (36.2 grams, 368.2 mmol) diluted with 99.6 mL of water was slowly dropped at a rate in which the solution temperature in the flask was kept at 15° C. or lower. After the reaction at 20° C. for 2 hours, the pH (20° C.) of the reaction mixture was 1. The reaction mixture was extracted three times with MIBK (100 mL). The organic layers were combined and washed with 20 mass % brine (100 mL). The solvent was removed from the organic layers using an evaporator, and 100 mL of toluene was added to the obtained solid, which was then heated to 40° C. to be dissolved in toluene. The solution was cooled to 5° C. at a programmed rate of 10° C./hr for crystallization. The deposited crystals were filtered, and dried at 30° C. under reduced pressure. Accordingly, lactone compound (C-1) was obtained (7.1 grams at 30.9% yield).

chemical formulas 31

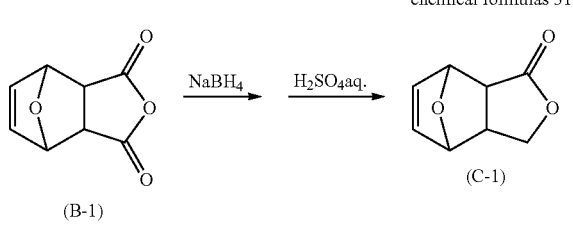

<1-2 Hydroboration Process>

In a flask with attached dropping funnel, cooling tube, thermometer, nitrogen gas inlet and stirrer, lactone compound (C-1) (6.09 grams, 40.0 mmol) and sodium borohydride (1.51 grams, 40.0 mmol) were added and purged with nitrogen. Nitrogen was kept flowing during reactions. Next, DME (80 mL) was added while the flask was cooled. Meanwhile, 95 mass % sulfuric acid (2.06 grams, 20 mmol) was measured in a dropping funnel and slowly dropped out in 30 minutes so that the temperature in the flask was kept at 15° C. or lower. After the completion of dropping, the temperature was raised to 20° C. and the reaction mixture was continued to be stirred for 4 hours. During that time, sodium borohydride was reacted with sulfuric acid and DME and became a $B_2H_6$.DME complex to act accordingly.

After the reaction was completed, the reaction mixture was cooled to 5° C., water (1 mL) was added to the mixture, and a 3M-NaOH solution was further added (5.44 mL). A 30 mass % hydrogen peroxide solution (5.44 mL) was dropped into the reaction mixture at a slow rate so that the temperature in the flask was kept under 20° C. After the dropping was completed, the reaction mixture was heated and stirred at 50° C. for an hour. Next, after the reaction mixture was cooled to 20° C., a 30 mass % sulfuric acid solution was added to set the pH (at 20° C.) of the reaction mixture at 1, and then the mixture was neutralized by a 3M sodium hydroxide solution to set the pH at 7. The reaction mixture was concentrated by an evaporator and 50 mL of acetonitrile was added. As crystallized sodium sulfate was deposited, the deposit was removed by filtration under reduced pressure. Then, the filtrate was concentrated, and 50 mL of acetonitrile was added again and concentrated. Those procedures were repeated twice. As a result, crude alcohol compound (D-1) was obtained (3.5 grams, crude yield at 51.4%). The moisture in the crude compound was 1800 ppm. The obtained crude compound was used for the subsequent step without being purified.

chemical formula 32

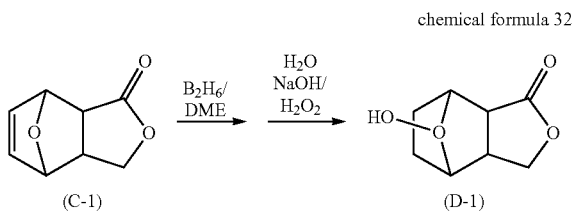

<1-3 Esterification>

In a flask with attached dropping funnel, thermometer, calcium chloride tube and stirrer, the crude alcohol compound (D-1) (0.50 grams, 2.94 mmol), acetonitrile (3.8 mL) and triethylamine (0.33 grams, 3.23 mmol) were added and the temperature in the flask was set at 20° C.

Methacrylic acid chloride (0.34 grams, 3.25 mmol) separately measured was slowly dropped and reacted at 20° C. for 4 hours. After the reaction was completed, 5.0 mL of water was added, and the reaction mixture was extracted three times with ethyl acetate (5.0 mL). The organic layers were combined and washed with 20 mass % brine. The organic layers were concentrated by an evaporator, and purified by silica gel column chromatography. Accordingly, compound (A-1) was obtained (1.01 grams, 72.0% yield, 99 mass % purity).

chemical formula 33

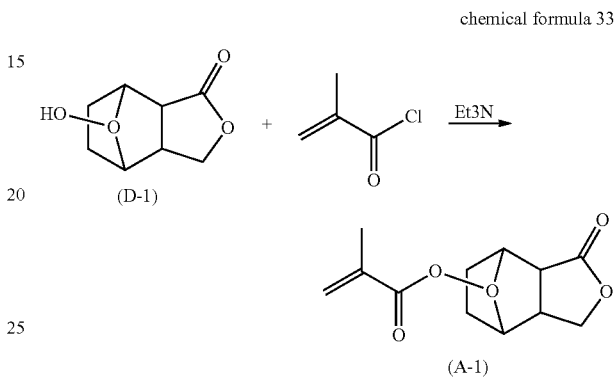

Comparative Example A1

A reduction process was conducted in the same manner as in example A1 and lactone compound (C-1) was obtained.

In a flask with attached dropping funnel, thermometer, reflux condenser and stirrer, lactone compound (C-1) (1.33 grams, 8.74 mmol) and formic acid (2.98 grams, 64.9 mmol) were added and stirred. Trifluoromethanesulfonic acid (0.252 grams, 1.68 mmol) measured separately in the dropping funnel was slowly added with careful attention to heat. After the reaction mixture in the flask was heated to 100° C., the mixture was stirred at 100° C. for 6 hours. As a result, namely, under an acid catalyst, when lower carboxylic acid was added to obtain an alcohol compound by hydrolysis, lactone compound (C-1) completely disappeared, but the targeted formic acid adduct was not produced at all.

Comparative Example A2

A reduction process was conducted in the same manner as in example A1 and lactone compound (C-1) was obtained.

In a flask with attached dropping funnel, thermometer, reflux condenser and stirrer, lactone compound (C-1) (1.33 grams, 8.74 mmol) and methacrylic acid (3.01 grams, 35.0 mmol) were added and stirred. In the mixture, 95 mass % sulfuric acid (0.18 grams, 1.75 mmol) measured separately in the dropping funnel was slowly added with careful attention to heat. After the reaction mixture in the flask was heated to 85° C., the mixture was stirred at 85° C. for 4 hours. As a result, namely, when methacryloyl was directly obtained without producing an alcohol compound, lactone compound (C-1) completely disappeared, but the targeted methacrylic acid adduct was not produced at all.

Example A2

In a flask with attached condenser, thermometer, air bubbling inlet and stirrer, 2.2 grams (0.12 mol) of alcohol compound (D-1) synthesized by the same method as in example D1 was dissolved in 9.4 grams of 1,2-dimethoxyethane, and 5 mg of dibutyl hydroxy toluene and 3.0 grams (0.19 mol) of methacrylic anhydride were added, and 0.26 grams (0.06 mol) of magnesium oxide was further added. The temperature of the reaction mixture was raised to 70° C. while creating air bubbles, the reaction mixture was heated and stirred for 8 hours.

The reaction mixture was dissolved in 16 grams of toluene, and 0.8 mg of 4-hydroxy-2,2,6,6-tetramethylpiperidine-1-oxyl free radical was added and dissolved. Then, the mixture was filtered and concentrated under reduced pressure until the weight reached 21 grams. The concentration was washed with 8 grams of water, and 16 grams of toluene was added again to the water phase, and the target product was collected. Those two toluene phases were combined and washed twice with 8 grams of saturated sodium bicarbonate and three times with 8 grams of water. After 1 mg of 4-hydroxy-2,2,6,6-tetramethylpiperidine-1-oxyl free radical and 2 mg of dibutyl hydroxyltoluene were added, the mixture was concentrated under reduced pressure.

Accordingly, 2.2 grams of target compound (A-1) was obtained (73% yield). The peak area of impurity (X) with a molecular weight of 308 in compound (A-1) was 0.1% relative to the peak area of compound (A-1). No methacrylic acid was detected.

Impurity (X) with a molecular weight of 308 in compound (A-1) was analyzed under conditions below (the same applies to the other examples). Impurity (X) is a compound detected in about 16.8 minutes.
  column: Zorbax XDB-C18, 3.5 μm, 2.1 mm×150 mm (made by Agilent Technologies Inc.)
  mobile phase: water/acetonitrile gradient 90/10→0/100 (30 minutes).
  detector: UV (210 nm).

Example A3

Reaction and purification procedures were conducted by the same method as in example A2, except that the alcohol compound (D-1) synthesized the same as in example D2 was used instead of the alcohol compound (D-1) synthesized the same as in example D1. As a result, 1.9 grams of target compound (A-1) was obtained (63% yield).

The peak area of impurity (X) with a molecular weight of 308 in compound (A-1) was 0.2% relative to the peak area of compound (A-1). No methacrylic acid was detected.

Example A4

In a flask with attached dropping funnel, thermometer, calcium chloride tube and stirrer, 2.2 grams (0.12 mol) of alcohol compound (A-1) synthesized by the same method as in example D1 was placed and dissolved in 9.4 grams of 1,2-dimethoxyethane, and then 5 mg of dibutyl hydroxy toluene and 2.0 grams (0.02 mol) of triethylamine were added and the temperature in the flask was adjusted to 5° C. Into the mixture, 2.1 grams (0.02 mol) of methacrylic acid chloride measured separately was slowly dropped and reacted at 5° C. for an hour. After the reaction was finished, 19 grams of water was added to the reaction mixture so that excess methacrylic acid chloride was decomposed.

As a result of purifying the reaction mixture the same as in example A2, 1.5 grams of the target compound was obtained (50% yield).

The peak area of impurity (X) with a molecular weight of 308 in compound (A-1) was 0.3% relative to the peak area of compound (A-1). No methacrylic acid was detected.

Production Example of Polymer (P)

Production Examples P1, P2 and P3

Monomers (a), (d), (e) and (f) respectively represented by formulas (a), (d), (e) and (f) were copolymerized to produce polymers (P).

In production example P1, methacrylate ester (A-1) obtained in example A2 was used as monomer (a).

In production example P2, methacrylate ester (A-1) obtained in example A3 was used as monomer (a).

In production example P3, methacrylate ester (A-1) obtained in example A4 was used as monomer (a).

Table 3 shows the amounts of impurity (X) with a molecular weight of 308 in monomers (a) used respectively (methacrylate esters (A-1)). Monomers (d), (e) and (f) in their respective lots were used.

chemical formulas 34

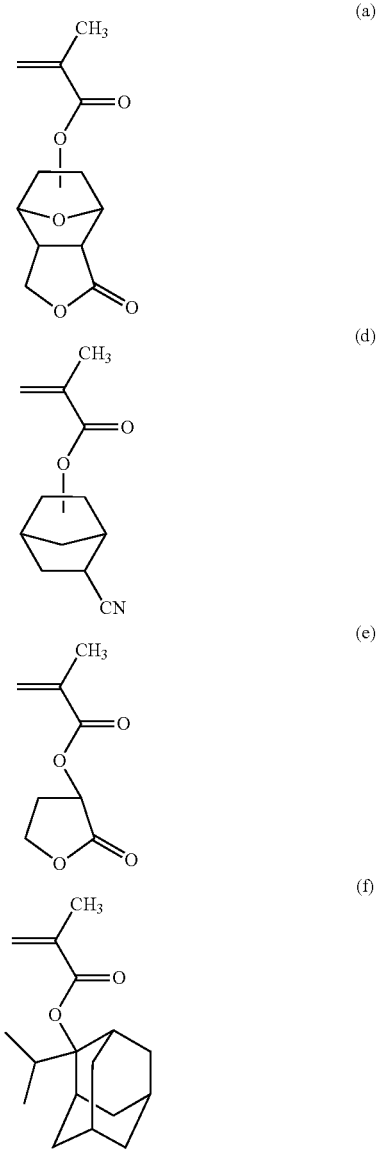

In a flask with attached nitrogen inlet, stirrer, condenser, dropping funnel and thermometer, 41.2 parts by mass of ethyl lactate and 23.2 parts by mass of γ-butyrolactone were placed under nitrogen atmosphere. The flask was put into a water bath, and the temperature of the water bath was raised while the contents of the flask were stirred until the mixture temperature in the flask reached 80° C.

Then, the mixture below was dropped out in 4 hours from the dropping funnel, and a temperature of 80° C. was retained for 3 hours. As a result, a reaction mixture was obtained.

(mixture)
monomer (a): 8.09 parts by mass,
monomer (d): 6.97 parts by mass,
monomer (e): 5.78 parts by mass,
monomer (f): 17.82 parts by mass,
ethyl lactate: 43.8 parts by mass,
γ-butyrolactone: 46.4 parts,
dimethyl-2,2'-azobisisobutyrate (brand name V601 made by Wako Pure Chemical Industries, Ltd.): 1.173 parts by mass.

While stirring, the obtained mixture was dropped into a mixed solvent of methanol and water (methanol/water at 80:20 volume ratio) approximately six times the volume of the obtained mixture. As a result, white sediment (polymer (P)) was formed. The sediment was filtered and the reaction mixture was again dropped into a mixed solvent of methanol and water (methanol/water at 90:10 volume ratio) approximately six times the volume of the obtained mixture, and the sediment was washed while the mixture was being stirred. Then, the sediment after washing was filtered to obtain wet polymer powder. Regarding polymer (P) obtained by drying under reduced pressure for approximately 36 hours at 60° C., the ratio (unit:mol %) of structural units (a), (d), (e) and (f) derived respectively from monomers (a), (d), (e) and (f) and methacrylic acid (MAA) as an impurity were measured using nuclear magnetic resonance spectrometry ($^1$H-NMR). The results are shown in Table 3.

TABLE 3

| | amount of impurity (X) in monomer (a) (area %) | composition ratio at mol % (1H_NMR) | | | | |
|---|---|---|---|---|---|---|
| | | (a) | (e) | (f) | (d) | MAA |
| production example P1 | 0.1% | 27.3 | 25.0 | 32.7 | 14.6 | 0.2 |
| production example P2 | 0.2% | 27.3 | 24.8 | 32.7 | 13.9 | 0.4 |
| production example P3 | 0.3% | 27.3 | 24.8 | 32.7 | 13.9 | 1.3 |

From the results in Table 3, it was found that if impurity (X) with a molecular weight of 308 was contained more in monomer (a), more methacrylic acid, produced when the monomer is decomposed, was detected in polymer (P). Especially, production examples (P1, P2) were found to have less methacrylic acid.

Production Method of Compound (iii)

Example F1

In the present example, compound (iii-1) was prepared from a compound represented by formula (ii-1).

chemical formulas 35

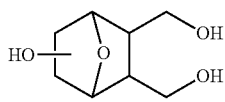
(ii-1)

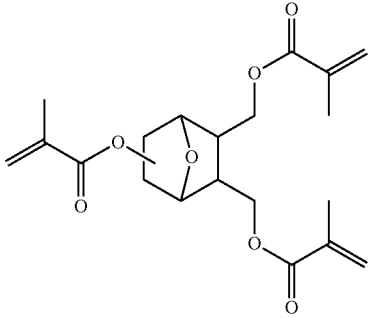
(iii-1)

(Synthesis of Compound Represented by Formula (ii-1))

In a flask with attached thermometer, calcium chloride tube and stirrer, 11.3 grams (0.3 mol) of sodium borohydride and 20 grams of dimethoxyethane were placed and cooled to 5° C. while the mixture was being stirred to obtain slurry (A) in which sodium borohydride was partially dissolved. In a beaker, 10 grams (0.06 mol) of a compound represented by formula (B-1), 3 grams of methanol and 100 grams of dimethoxyethane were placed to obtain slurry (B) in which the contents were partially dissolved. Slurry (B) was slowly dropped into slurry (A), which was being cooled and stirred, so that the liquid temperature did not exceed 10° C. After the reaction mixture was kept stirred at room temperature for a full day, a 20 mass % sulfuric acid solution was added to neutralize the mixture while it was cooled (pH 6.5 at 20° C.).

The solvent and moisture were mostly removed using an evaporator to obtain powder, to which 200 grams of ethanol was added to form a suspension. Next, the suspension was filtered and the filtrate was concentrated to obtain an oil-like material, to which 500 mL of acetone was added to partially dissolve the oil-like material. Then, the mixture was partially dissolved and settled until an acetone phase and an oil phase were separated. The acetone phase was filtered and concentrated, and such procedures were repeated six times.

As a result, 4.4 grams of a compound represented by formula (ii-1) was obtained. The compound contained a slight amount of borate.

(Synthesis of Compound Represented by Formula (iii-1)

In a flask with attached thermometer, stirrer and air inlet tube, 1.7 grams of a compound represented by formula (ii-1), 4.1 mg of BHT, 9.3 grams (0.06 mol) of methacrylic anhydride and 0.48 grams (0.12 mol) of magnesium oxide were placed and stirred. Next, the temperature of the mixture was raised to 70° C. and reactions were carried out for 8 hours. Then, the temperature was cooled to 50° C., and 3.6 mL of methanol was added to the mixture, which was stirred at 50° C. for 2 hours. Those procedures were carried out while creating a small amount of air bubbles. The mixture was cooled and filtered. Then, 2 mg of 4-hydroxy-2,2,6,6-tetramethylpiperidine-1-oxyl free radical was added and the filtrate was concentrated using an evaporator. The concentrate was dissolved in 15 mL of toluene, and washed with 7.5 grams of water. Toluene was added to the water phase at that time to carry out extraction. Two toluene phases were combined and washed six times with 10 mL of saturated sodium bicarbonate and twice with 10 mL of water. The toluene phase was concentrated and purified using a silica gel column (a solution containing hexane and ethyl acetate at a ratio of 6 to 1) to obtain 2.1 grams of a compound represented by formula (iii-1) (oil-like material with an area percentage of 99% by liquid chromatography).

FIG. 1 is an $^1$H-NMR spectrum of a compound (iii-1) obtained in the present example.

Figure 2:
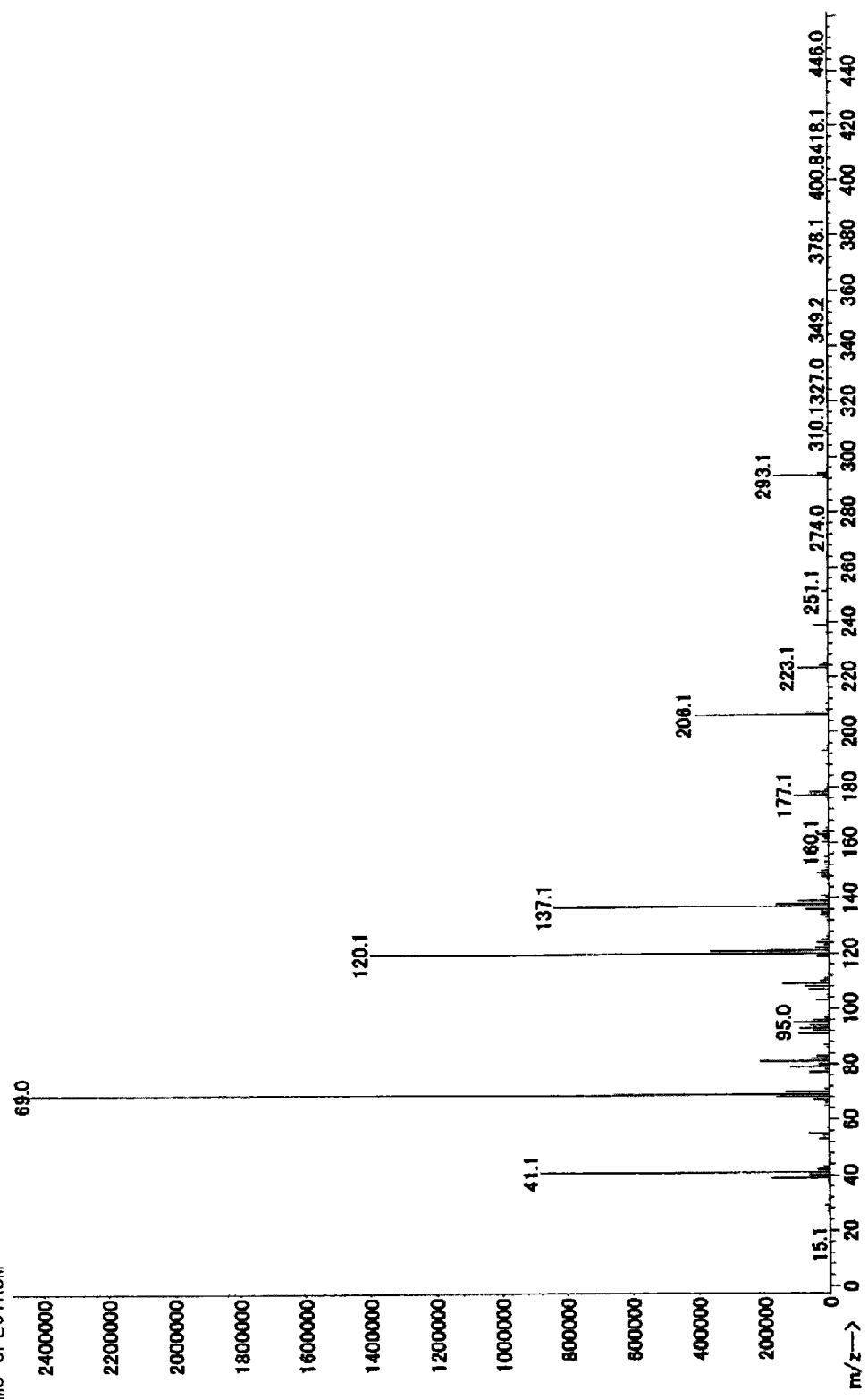
FIG. 2 is MS spectrum of compound (iii-1) obtained in the example.

FIG. 2 is an MS spectrum of a compound (iii-1) obtained in the present example.

Test Examples 1 to 5

To study the influence of a compound (iii) as an impurity when contained in (meth)acrylate ester as a monomer, a polymer was prepared by adding a predetermined amount of a compound (iii-1) prepared in example F1.

Monomers used in the present examples were monomers (a) to (d) respectively represented by formulas (a) to (d).

Methacrylate ester (A-1) obtained in example (A1) was used as monomer (a). The compound (iii) in monomer (a) was not detected. A compound (iii-1) prepared in example (F1) was used as monomer (b). As monomers (c) and (d), monomers in their respective lots were used.

chemical formulas 36

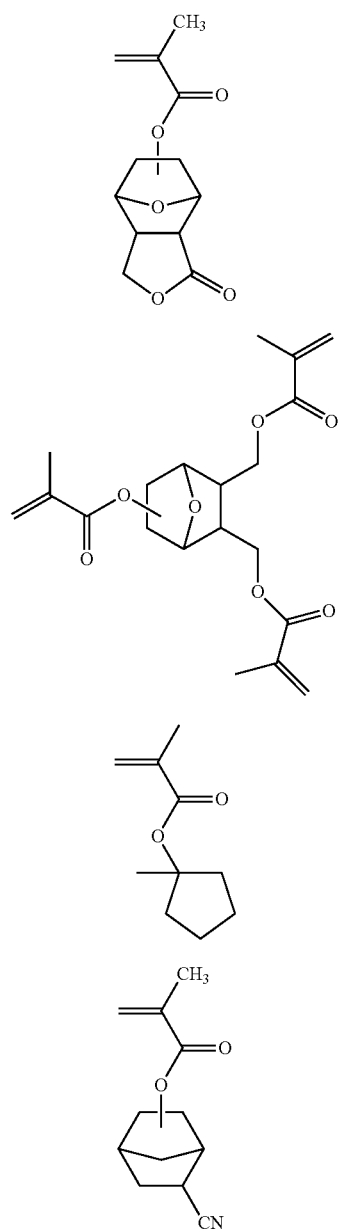

Namely, 1.55 parts of ethyl lactate and 1.04 parts of polymerization initiator V-601 HP230 were put into a sealed container and dissolved. In a flask with attached nitrogen inlet, stirrer, condenser and thermometer, 12.6 parts by mass of ethyl lactate and 9.4 parts by mass of γ-butyrolactone were added, to which monomers were added in the amounts specified in table 4. After nitrogen bubbling was conducted for 30 minutes, the flask was placed in a water bath to initiate a temperature rise so that the liquid temperature in the flask was raised to 80° C. A polymerization initiator solution was added to the mixture, which was kept at 80° C. for 4 hours. Those procedures were conducted while the mixture was stirred under nitrogen current.

The obtained reaction mixtures were each put through a GPC (gel permeation chromatograph) to measure their weight average molecular weight. The results are shown in table 4.

(GPC Conditions)
column: Shodex GPC KF-801 (made by Showa Denko K.K.), two columns.
temperature: 40° C.
flow rate: 1.0 mL/min
mobile phase: tetrahydrofuran
detector: differential refractive index detector (RI)

Also, 160 grams of methanol was added to the entire reaction mixture to settle a polymer. The sedimentation was filtered to obtain a polymer wet powder, which was then dried at 60° C. for 36 hours. Accordingly, a polymer was obtained.

The dried polymer was dissolved in a mixed solution of 10 mass % of 2-butanone and 90 mass % of propylene glycol monomethyl ether acetate, and its turbidity (unit: NTU) was measured at 27° C.

Turbidities were measured three times by a turbidimeter (brand name TB200 made by Orbeco-Hellige Inc.) and the average value was obtained. The results are shown in table 5.

TABLE 4

| test example | monomer composition (parts by mass) | | | | weight-average molecular weight | amount of (b) to (a) |
|---|---|---|---|---|---|---|
| | (a) | (b) | (c) | (d) | | |
| 1 | 2.14 | 0 | 2.52 | 1.23 | 10400 | 0 |
| 2 | 2.08 | 0.06 | 2.52 | 1.23 | 16000 | 3 mass % |
| 3 | 2.01 | 0.13 | 2.52 | 1.23 | 29300 | 6 mass % |
| 4 | 1.95 | 0.19 | 2.52 | 1.23 | 84400 | 9 mass % |
| 5 | 1.88 | 0.26 | 2.52 | 1.23 | 119500 | 12 mass % |

TABLE 5

| | turbidity (NTU) test example | | | | |
|---|---|---|---|---|---|
| amount of (b) to (a) (mass %) | 1 | 2 | 3 | 4 | 5 |
| | 0% | 3% | 6% | 9% | 12% |
| first | 1.8 | 2.3 | 4.2 | 9.6 | 18.9 |
| second | 1.8 | 2.3 | 4.3 | 9.6 | 18.9 |
| third | 1.8 | 2.3 | 4.3 | 9.6 | 18.9 |
| average | 1.8 | 2.3 | 4.3 | 9.6 | 18.9 |

From the results shown in tables 4 and 5, it is found that when the amount of compound (iii) as monomer (b) becomes 9 mass % or greater relative to methacrylate ester (A) as monomer (a), the weight-average molecular weight of the polymer increases significantly, and its turbidity also increases significantly.

What is claimed is:

1. A method for producing an alcohol compound represented by formula (D), the method comprising:
   a hydroboration process comprising reacting in a solvent a compound represented by formula (C) and a boron agent that is a borane dimethylsulfide complex or a borane-1,2-dimethoxyethane complex, to obtain a reaction mixture; and
   an oxidation process comprising treating the reaction mixture with hydrogen peroxide, and then adjusting a pH of the reaction mixture to be within a range of 0.5 to 4:

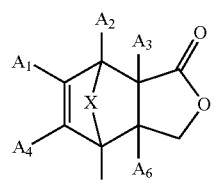

(C)

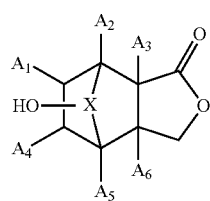

(D)

wherein:
$A_1$ to $A_6$ are each independently a hydrogen atom, methyl group or ethyl group; and
X is an oxygen atom, sulfur atom, methylene group or ethylene group.

2. The method of claim 1, wherein the boron agent is a borane dimethylsulfide complex.

3. The method of claim 1, further comprising isolating the alcohol compound represented by formula (D) by recrystallizing the reaction mixture by adjusting the pH of the reaction mixture to be 5 to 9 after the oxidation process.

4. The method of claim 1, further comprising forming the compound represented by the formula (C) by reducing a compound represented by formula (4) with sodium borohydride,
   wherein an amount of sodium borohydride is set at a mole ratio of 0.7 to 0.95 relative to the compound represented by formula (4):

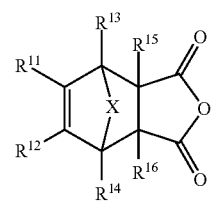

(4)

wherein $R^{11}$ to $R^{16}$ are each independently a hydrogen atom, methyl group or ethyl group; and X is an oxygen atom, sulfur atom, methylene group or ethylene group.

5. A method for producing a (meth)acrylate ester, the method comprising:
   producing an alcohol compound represented by formula (D) from a compound represented by formula (C) by the method according to claim 1; and
   performing an esterification reaction of the compound represented by formula (D) to obtain a (meth)acrylate ester represented by formula (A):

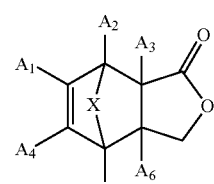

(C)

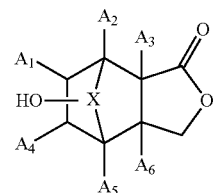

(D)

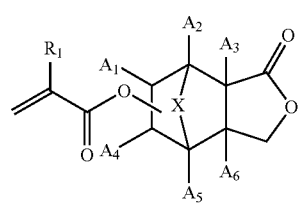

(A)

wherein in all of formulae (A), (C), and (D) $R_1$ is a hydrogen atom or a methyl group, $A_1$ to $A_6$ are each independently a hydrogen atom, methyl group or ethyl group, and X is an oxygen atom, sulfur atom, methylene group or ethylene group.

6. The method of claim 5, further comprising, prior to said producing an alcohol compound represented by formula (D), forming the compound represented by the formula (C) by reducing a compound represented by formula (4) with sodium borohydride,
   wherein an amount of sodium borohydride is set at a mole ratio of 0.7 to 0.95 relative to the compound represented by formula (4):

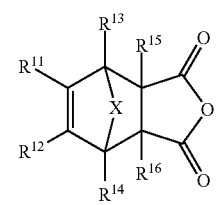

(4)

wherein $R^{11}$ to $R^{16}$ are each independently a hydrogen atom, methyl group or ethyl group; and X is an oxygen atom, sulfur atom, methylene group or ethylene group.

7. The method of claim 1, wherein the boron agent is a borane-1,2-dimethoxyethane complex.

8. The method of claim 1, wherein X is an oxygen atom.

9. The method of claim 1, wherein X is a sulfur atom.

10. The method of claim 1, wherein X is a methylene group.

11. The method of claim 1, wherein X is an ethylene group.

* * * * *